United States Patent
Nanduri et al.

(10) Patent No.: US 7,119,188 B2
(45) Date of Patent: Oct. 10, 2006

(54) N-CARBOBENZYLOXY (N-CBZ)-DEPROTECTING ENZYME AND USES THEREFOR

(75) Inventors: Venkata B. Nanduri, East Brunswick, NJ (US); Ramesh N. Patel, Bridgewater, NJ (US); Steven L. Goldberg, Basking Ridge, NJ (US); Robert M. Johnston, Whitehouse Station, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 23 days.

(21) Appl. No.: 10/453,418

(22) Filed: Jun. 3, 2003

(65) Prior Publication Data

US 2006/0149047 A1 Jul. 6, 2006

Related U.S. Application Data

(63) Continuation-in-part of application No. 10/017,711, filed on Dec. 14, 2001, now Pat. No. 6,828,119.

(60) Provisional application No. 60/259,715, filed on Jan. 4, 2001.

(51) Int. Cl.
*C07H 21/04* (2006.01)
*C12N 9/14* (2006.01)
*C12N 1/20* (2006.01)
*C12N 15/00* (2006.01)

(52) U.S. Cl. .................... 536/23.2; 435/195
(58) Field of Classification Search .............. 435/195; 536/23.2
See application file for complete search history.

(56) References Cited

U.S. PATENT DOCUMENTS

| 5,508,272 A | 4/1996 | Robl ........................... 514/80 |
| 5,552,397 A | 9/1996 | Karanewsky et al. .. 514/212.03 |

FOREIGN PATENT DOCUMENTS

| WO | WO00/47207 | 8/2000 |
| WO | WO 02/053724 | 12/2001 |

OTHER PUBLICATIONS

Witkowski et al, Conversion of a beta-ketoacyl synthase to a malonyl decarboxylase by replacement of the active-site cysteine with glutamine. Biochemistry. Sep. 7, 1999;38(36):11643-50.*
Wishart et al, A single mutation converts a novel phosphotyrosine binding domain into a dual-specificity phosphatase. J Biol Chem. Nov. 10, 1995;270(45):26782-5.*
Molecular cloning, nucleotide sequence, and expression of a carboxypeptidase-encoding gene from the archaebacterium *Sulfolobus solfataricus*. J Bacteriol. Oct. 1995;177(19):5561-6.*
UniProt DataBase Acc#CBP1_SULSO Oct. 1, 1996 Colombo et al. Alignment with SEQ ID No. 2.*
Stedman's Medical Dictionary 26th Edition, Williams & Wilkins Baltimore. pp. 1497-1498.*
Witkowski et al, Conversion of a beta-ketoacyl synthase to a malony decarboxylase by replacement of the active-site cysteine with glutamine. Biochemistry. Sep. 7, 1999;38(36):11643-11650.*
Wishart et al, A single mutation converts a novel phosphotyrosine binding domain into a dual-specificity phosphatase. J Biol Chem. Nov. 10, 1995;270(45):26782-26785.*
Green and Wuts, Protective Groups In Organic Synthesis, John Wiley & Sons, NY, 1991. pp. 307-348.
Jeyaraj et al., Tetrahedron Letters 42 (2001) pp. 835-837.
Pohl et al., J. Am. Chem. Soc. 119, (1997) pp. 6702-6710.
Kappes et al., Carbohydrate Research 305 (1998) pp. 341-349.
Pohl et al., Tetrahedron Letters, vol. 36, No. 17, (1995) pp. 2963-2966.
Theodoridis, G., Tetrahedron 56 (2000) pp. 2239-2358..
Waldmann et al., 277 Chemical Reviews, American Chemical Society, 94 (Jun. 1994), No. 4, pp. 911-937.

* cited by examiner

*Primary Examiner*—Sheridan Swope
(74) *Attorney, Agent, or Firm*—Audrey Sher; Nickki L. Parlet

(57) ABSTRACT

This invention relates to isolated or recombinant N-carbobenzyloxy-deprotecting enzyme polypeptides, and variants and fragments thereof, that catalyze the removal of carbobenzyloxy from carbobenzyloxy-protected amino acids and alcohols. Also related are isolated nucleic acids encoding N-carbobenzyloxy-deprotecting enzyme polypeptides, and variants, and fragments thereof, as well as vectors and host cells comprising these nucleic acids. The invention also relates to methods of obtaining isolated nucleic acids, polypeptides, and antibodies, and methods of using the polypeptides in various reactions for industrial or pharmaceutical applications.

15 Claims, No Drawings

US 7,119,188 B2

N-CARBOBENZYLOXY (N-CBZ)-DEPROTECTING ENZYME AND USES THEREFOR

This application is a continuation-in-part of U.S. application Ser. No. 10/017,711, filed Dec. 14, 2001 issued as U.S. Pat. No. 6,828,119 on Dec. 7, 2004, which claims the benefit of U.S. Provisional Application Ser. No. 60/259,715, filed Jan. 4, 2001.

FIELD OF THE INVENTION

This invention relates to a novel N-carbobenzyloxy-deprotecting enzyme, isolatable from *Sphingomonas paucimobilis*, which catalyzes the removal of carbobenzyloxy (CBZ) from N—CBZ protected amino acids and O—CBZ protected alcohols. The invention also relates to isolated nucleic acids comprising nucleotide sequences which encode N-carbobenzyloxy-deprotecting enzyme polypeptides, vectors and host cells comprising these nucleic acids, isolated N-carbobenzyloxy-deprotecting enzyme polypeptides, recombinant N-carbobenzyloxy-deprotecting enzyme polypeptides, and antibodies that specifically bind to N-carbobenzyloxy-deprotecting enzyme polypeptides. The invention further relates to methods of obtaining isolated N-carbobenzyloxy-deprotecting enzyme nucleic acids, isolated polypeptides, recombinant polypeptides, and antibodies, and to methods of producing N-carbobenzyloxy-deprotecting enzyme with the vectors and host cells, and to methods of using N-carbobenzyloxy-deprotecting enzyme in reactions required for the synthesis of industrial or pharmaceutical compounds.

BACKGROUND OF THE INVENTION

Carbobenzyloxy (CBZ) group is commonly used to protect amino and hydroxide groups during organic synthesis. Other similar "carbamate" and "carbonate" protecting groups are also used to protect amino and hydroxyl groups. Chemical deprotection is usually achieved by methods such as hydrogenation with palladium catalyst. However, if other groups are present which are susceptible to the deprotection condition (for example, sulfur during hydrogenation), alternative methods of deprotection are necessary. It would be beneficial to have alternate methods of deprotection that would not destroy susceptible groups. An enzymatic method of deprotection using *S. paucimobilis* N-carbobenzyloxy-deprotecting enzyme isolated from soil samples has been disclosed in WO 02/053724, which application shares a priority claim with this application. The enzymatic method can be conducted under mild conditions (i.e., aqueous medium at room temp and atmospheric pressure) and without the destroying susceptible groups. Given the importance of the enzyme and its relatively low presence in the host bacterium, it would be useful to clone and express in a heterologous host such as *Escherichia coli* to ensure a sufficient supply for large-scale reactions.

SUMMARY OF THE INVENTION

It is an object of the present invention to provide novel N-carbobenzyloxy-deprotecting enzyme polypeptides, and variants, modifications, and fragments thereof. N-carbobenzyloxy-deprotecting enzyme is herein also referred to as N—CBZ-deprotecting enzyme. An N—CBZ-deprotecting enzyme polypeptide has been isolated from *S. paucimobilis*.

It is also an object of the invention to provide isolated N—CBZ-deprotecting enzyme polynucleotides, e.g., DNA and RNA molecules, comprising nucleotide sequences encoding N—CBZ-deprotecting enzyme polypeptides and complementary sequences thereof, as well as nucleic acid variants, modifications, fragments thereof.

It is a further object of the present invention to provide nucleic acid probes and primers, as well as vectors and host cells, comprising polynucleotides of the invention.

It is yet a further object of the present invention to provide isolated N—CBZ-deprotecting enzyme polypeptides and polypeptide fragments, variants, and modifications thereof.

It is yet a further object of the present invention to provide recombinant N—CBZ-deprotecting enzyme polypeptides, and polypeptide fragments, variants, and modifications thereof.

It is another object of the present invention to provide antibodies and antibody fragments that specifically bind to the polypeptides, or polypeptide variants, modifications, or fragments thereof.

It is yet another object of the present invention to provide methods of using the polynucleotides, vectors, and host cells of the invention to produce polypeptides of the invention, such as N—CBZ-deprotecting enzyme polypeptides.

It is still another object of the present invention to provide methods of using the polypeptides of the invention, such as N—CBZ-deprotecting enzyme polypeptides, in enzymatic reactions requiring the deprotection of an amino or hydroxyl group. In various aspects, this process uses isolated polypeptide, or cell-free extracts or whole cells expressing recombinant polypeptide.

It is a further object of the present invention to provide methods of purifying the N—CBZ-deprotecting enzyme polypeptides, or polypeptide variants, modifications, or fragments thereof, using the disclosed antibodies or antibody fragments.

It is still another object of the present invention to provide a method of deprotecting an amine or alcohol protected with a group of formula

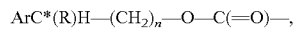

where the substituents are as described below, the method comprising: contacting the protected amine or alcohol with an enzyme effective to remove the protecting group; and recovering the amine or alcohol.

It is also an object of the present invention to provide a method of isolating a bacteria producing an enzyme effective to remove a protecting group comprising: growing prospective bacteria on a medium having a growth selective amount of an amine compound that is protected as above; and isolating bacteria that grow on said medium.

It is still another object of the present invention to provide a method of resolving a desired enantiomer of an amine or alcohol linked to a chiral carbon comprising: providing a derivative of the compound in which the amine or alcohol is protected with a group of formula ArC*(R)H—(CH$_2$)$_n$—O—C(=O)—; contacting the protected compound with an enzyme effective to remove the protecting group; and isolating the compound or protected derivative thereof in a composition that is enantiomerically enriched in the desired enantiomer.

Additional objects and advantages afforded by the present invention will be apparent from the detailed description and exemplification hereinbelow.

DETAILED DESCRIPTION OF THE INVENTION

The present invention relates to isolated nucleic acids that comprise the protein-coding regions for an N—CBZ-deprotecting enzyme. The present invention also relates to isolated and recombinant polypeptides encoded by these regions. Also related are isolated nucleic acids, isolated polypeptides, and recombinant polypeptides comprising variants, modifications and fragments of the disclosed sequences, as well as reagents (e.g., probes, primers, vectors, and antibodies) relating to these sequences. The nucleic acids and polypeptides of the present invention are useful for various biotechnology and pharmaceutical applications as disclosed in detail herein. The present invention also relates to various methods employing the proteins and nucleic acids of the invention.

Definitions

Use of the terms "SEQ ID NO:6–SEQ ID NO:15" etc., is intended, for convenience, to refer to each individual SEQ ID NO individually, and is not intended to refer to the sequences collectively. The invention encompasses each sequence individually, as well as any combination thereof.

"Nucleic acid or "polynucleotide" as used herein refers to purine- and pyrimidine-containing polymers of any length, either polyribonucleotides or polydeoxyribonucleotide or mixed polyribo-polydeoxyribonucleotides. This includes single- and double-stranded molecules, i.e., DNA—DNA, DNA-RNA and RNA—RNA hybrids, as well as "protein nucleic acids" (PNA) formed by conjugating bases to an amino acid backbone. This also includes nucleic acids containing modified bases. Polynucleotides, e.g., oligonucleotides, include naturally-occurring species or synthetic species formed from naturally-occurring subunits or their close homologs. The term may also refer to moieties that function similarly to polynucleotides, but have non-naturally-occurring portions. Thus, polynucleotides may have altered sugar moieties or inter-sugar linkages. Exemplary among these are phosphorothioate and other sulfur containing species which are known in the art.

A "coding sequence" or a "protein-coding sequence" is a polynucleotide sequence capable of being transcribed into mRNA and/or capable of being translated into a polypeptide. The boundaries of the coding sequence are typically determined by a translation start codon at the 5'-terminus and a translation stop codon at the 3'-terminus.

A "complement" or "complementary sequence" of a nucleic acid sequence as used herein refers to the antisense sequence that participates in Watson-Crick base-pairing with the original sequence.

A "probe" or "primer" refers to a nucleic acid or oligonucleotide that forms a hybrid structure with a sequence in a target region due to complementarily of at least one sequence in the probe or primer with a sequence in the target region.

"Isolated", as used herein when referring to a nucleic acid, refers to a nucleic acid molecule which is one or both of the following: (1) not immediately contiguous with either one or both of the sequences, eg. coding sequences, with which it is immediately contiguous (i.e., one at the 5' end and one at the 3' end) in the naturally occurring genome of the organism from which the nucleic acid is derived; or (2) which is substantially free of a nucleic acid sequence with which it occurs in the organism from which the nucleic acid is derived. The term includes, for example, a recombinant DNA which is incorporated into a vector, eg. into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Isolated DNA also includes a recombinant DNA which is part of a hybrid gene encoding additional sequence. "Isolated", as used herein when referring to a polypeptide or protein, refers to a polypeptide or protein which is substantially free of the cellular material, culture medium, or other components. Such isolated polypeptides or proteins contain less than 50%, preferably less than 25%, more preferably less than 10%, and most preferably less than 1% of the components with which they were associated.

The term "vector" as used herein refers to a nucleic acid molecule capable of replicating itself and another nucleic acid molecule to which it has been linked. A vector, for example, can be a plasmid, recombinant virus, or transposon.

"Host" includes prokaryotes and eukaryotes. The term includes an organism or cell that is the recipient of a replicable vector.

A "recombinant" polypeptide or peptide refers to an amino acid sequence encoded by a nucleotide sequence of the invention and produced using a nucleic acid of the invention.

As used herein, the terms "protein" and "polypeptide" are synonymous. "Peptides" are defined as fragments or portions of polypeptides, preferably fragments or portions having at least one functional activity (e.g., catalytic or antigenic activity) as the complete polypeptide sequence.

The term "antigenic" refers to the ability of a molecule (e.g., a polypeptide or peptide) to bind to its specific antibody, or an antibody fragment, with sufficiently high affinity to form a detectable antigen-antibody complex.

A "sample" as used herein refers to a biological sample, for example, cells, cell culture media, cell components (e.g., cell membranes or cellular organelles), cell extracts (e.g., cytoplasm, cytosol, or nuclear extracts), as well as samples obtained from, for example, a laboratory procedure.

The term "bioactive agent" as used herein refers to a substance such as a chemical that can act on a cell, virus, tissue, organ or organism, including but not limited to insecticides or drugs (i.e., pharmaceuticals) to create a change in the functioning of the cell, virus, organ or organism. Preferably, the organism is a mammal, more preferably a human.

The term "medium having a growth selective amount of a protected amine compound" as used herein refers to a medium in which the amount of any other amines other than the amine compound is less than an amount effective to promote bacterial growth in a growth-mediated selection process. Preferably, the protected amine is essentially the sole nitrogen source.

General descriptions of the foregoing terms and others are known in the art. See, e.g., Roitt et al., 1989, *Immunology*, 2$^{nd}$ Edition, C.V. Mosby Company, New York; Male et al., 1991, *Advanced Immunology*, 2nd Edition, Grower Medical Publishing, New York.

Nucleic Acids

One aspect of the present invention pertains to isolated N—CBZ-deprotecting enzyme nucleic acids, and variants, modifications, and fragments thereof. An N—CBZ-deprotecting enzyme nucleic acid comprises or consists of a nucleotide sequence encoding an N—CBZ-deprotecting enzyme polypeptide, such as the N—CBZ-deprotecting enzyme polypeptide of SEQ ID NO:2, or is a complement thereof. A preferred N—CBZ-deprotecting enzyme nucleic acid comprises or consists of one of the following sequences, or comprises or consists of a complement of one of the following sequences: SEQ ID NO:1; nucleotides 1–1278 of SEQ ID NO:1; SEQ ID NO:3; or the nucleotide sequence deposited as ATCC Accession Number PTA-5051. A preferred fragment, variant, or modification of a N—CBZ-deprotecting enzyme nucleic acid comprises a nucleic acid sequence encoding a functional equivalent of SEQ ID NO:2. Another preferred fragment, variant, or modification of a N—CBZ-deprotecting enzyme nucleic acid is useful as a primer or a probe. The nucleic acids of the invention can comprise at least 15, 20, 25, 50, 100, 200, 250, 300, 400, 500, 600, 700, 800, 900, 1000, 1100, or 1200 contiguous nucleotides. The nucleic acid molecules of the invention can be DNA or RNA. The nucleic acids of the invention are not limited to nucleic acids encoding proteins native to *Sphingomonas paucimobilis* or fragments thereof.

The term "functional equivalent" is intended to include nucleotide sequences encoding proteins that are variants, modifications or fragments of the N—CBZ-deprotecting enzyme polypeptide of SEQ ID NO:2 that perform at least one characteristic function of the N—CBZ-deprotecting enzyme polypeptide of SEQ ID NO:2, such as catalysis or antigenicity. A preferred functional equivalent is capable of deprotecting an N—CBZ-protected amino acid, where the conversion rate is preferably at least 10%, 20%, 30%, 40%, 50%, 60%, 70%, 80%, 85%, 90%, 95%, 99% or 100%. Preferably the N—CBZ-protected amino acid is an N—CBZ-protected L-amino acid, more preferably N—CBZ-L-phenylalanine, and the conversion rate is preferably at least 80%, 85%, 90%, 95%, 99%, or 100%. Exemplary deprotection assays are given the Examples herein, such as in Examples 4, 5, and 13. Additionally, deprotection can be assayed by the following assay.

An N—CBZ-protected D- or L-amino acid is incubated with an enzyme source at 28 to 45 degrees C. for 24 to 72 hours. The reaction is stopped by addition of 2 volumes of 50% acetonitrile. The samples are filtered and analyzed by HPLC.

DNA sequence polymorphisms within the nucleotide sequence of a nucleic acid, especially those within the third base of a codon, may result in "silent" mutations, which do not affect the encoded amino acid sequence of the polypeptide due to the degeneracy of the genetic code. Thus sequences differing from SEQ ID NO:1, and differing from nucleotides 1–1278 of SEQ ID NO:1, due to degeneracy of the genetic code are included in nucleic acids encoding SEQ ID NO:2. Because stop codons may vary without changing the amino acid sequence encoded, N—CBZ-deprotecting enzyme nucleic acids include nucleic acids comprising or consisting of nucleotides 1–1278 of SEQ ID NO:1.

Preferred embodiments include an isolated nucleic acid sharing at least 45, 50, 60, 70, 75, 80, 85, 90, 95, 99, or 100% sequence identity with an N—CBZ-deprotecting enzyme nucleic acid (e.g., SEQ ID NO:1 or a complement thereof). This polynucleotide sequence may be identical to the nucleotide sequence of SEQ ID NO:1, or may include up to a certain integer number of nucleotide alterations as compared to the reference sequence.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in Lesk, A. M. (Ed.), 1988, *Computational Molecular Biology*, Oxford University Press, New York; Smith, D. W. (Ed.), 1993, *Biocomputing. Informatics and Genome Projects*, Academic Press, New York; Griffin, A. M., and Griffin, H. G. (Eds.), 1994, *Computer Analysis of Sequence Data, Part I*, Humana Press, New Jersey; von Heinje, G., 1987, *Sequence Analysis in Molecular Biology*, Academic Press; Gribskov, M. and Devereux, J. (Eds.), 1991, *Sequence Analysis Primer*, M. Stockton Press, New York; and Carillo, H., and Lipman, D., 1988, SIAM *J. Applied Math.* 48:1073.

For nucleic acids, sequence identity can be determined by comparing a query sequences to sequences in publicly available sequence databases (NCBI) using the BLASTN2 algorithm (S. F. Altschul et al., 1997, *Nucl. Acids Res.*, 25:3389–3402). The parameters for a typical search are: E=0.05, v=50, B=50, wherein E is the expected probability score cutoff, V is the number of database entries returned in the reporting of the results, and B is the number of sequence alignments returned in the reporting of the results (S. F. Altschul et al., 1990, *J. Mol. Biol.*, 215:403–410).

In another approach, nucleotide sequence identity can be calculated using the following equation: % identity=(number of identical nucleotides)/(alignment length in nucleotides)*100. For this calculation, alignment length includes internal gaps but not includes terminal gaps. Alternatively, nucleotide sequence identity can be determined experimentally using the specific hybridization conditions described below.

In accordance with the present invention, nucleic acid alterations are selected from the group consisting of at least one nucleotide deletion, substitution, including transition and transversion, insertion, or modification (e.g., via RNA or DNA analogs, dephosphorylation, methylation, or labeling). Alterations may occur at the 5' or 3' terminal positions of the reference nucleotide sequence or anywhere between those terminal positions, interspersed either individually among the nucleotides in the reference sequence or in one or more contiguous groups within the reference sequence. Alterations of a nucleic acid sequence of (e.g., SEQ ID NO:1) may create nonsense, missense, or frameshift mutations in the coding sequence, and thereby alter the polypeptide encoded by the nucleic acid.

The present invention also encompasses naturally-occurring nucleotide polymorphisms of N—CBZ-deprotecting enzyme nucleic acids (e.g., SEQ ID NO:1). As will be understood by those in the art, the genomes of all organisms undergo spontaneous mutation in the course of their continuing evolution generating variant forms of gene sequences (Gusella, 1986, *Ann. Rev. Biochem.* 55:831–854). Restriction fragment length polymorphisms (RFLPs) include variations in DNA sequences that alter the length of a restriction fragment in the sequence (Botstein et al., 1980, *Am. J. Hum. Genet.* 32, 314–331). Short tandem repeats (STRs) include tandem di-, tri- and tetranucleotide repeated motifs, also termed variable number tandem repeat (VNTR) polymorphisms.

Single nucleotide polymorphisms (SNPs) are far more frequent than RFLPS, STRs, and VNTRs. SNPs may occur in protein coding (e.g., exon), or non-coding (e.g., intron, 5'UTR, and 3'UTR) sequences. SNPs in protein coding regions may comprise silent mutations that do not alter the amino acid sequence of a protein. Alternatively, SNPs in protein coding regions may produce conservative or non-conservative amino acid changes, described in detail below.

In non-coding sequences, SNPs may also result in defective protein expression (e.g., as a result of defective splicing). Other single nucleotide polymorphisms have no phenotypic effects.

Further encompassed by the present invention are nucleic acid molecules that share moderate homology with a N—CBZ-deprotecting enzyme nucleic acid (e.g., SEQ ID NO:1 or a complementary sequence), and hybridize to a N—CBZ-deprotecting enzyme nucleic acid under moderate stringency hybridization conditions. More preferred are nucleic acid molecules that share substantial homology with a N—CBZ-deprotecting enzyme nucleic acid (e.g., SEQ ID NO:1 or a complementary sequence) and hybridize to a N—CBZ-deprotecting enzyme nucleic acid under high stringency hybridization conditions.

As used herein, the phrase "moderate homology" refers to sequences which share at least 60% sequence identity with a N—CBZ-deprotecting enzyme sequence (e.g., SEQ ID NO:1 or a complementary sequence), whereas the phrase "substantial homology" refers to sequences that share at least 90% sequence identity with a N—CBZ-deprotecting enzyme sequence. It is recognized, however, that polypeptides and the nucleic acids encoding such polypeptides containing less than the above-described level of homology arising as splice variants or that are modified by conservative amino acid substitutions (or substitution of degenerate codons) are contemplated to be within the scope of the present invention.

The phrase "hybridization conditions" is used herein to refer to conditions under which a double-stranded nucleic acid hybrid is formed from two single nucleic acid strands, and remains stable. As known to those of skill in the art, the stability of the hybrid sequence is reflected in the melting temperature ($T_m$) of the hybrid (see F. M. Ausubel et al. (Eds.), 1995, *Current Protocols in Molecular Biology*, John Wiley and Sons, Inc., New York, N.Y.). The $T_m$ decreases approximately 0.5° C. to 1.5° C. with every 1% decrease in sequence homology. In general, the stability of a hybrid sequence is a function of the length and guanine/cytosine content of the hybrid, the sodium ion concentration, and the incubation temperature. Typically, the hybridization reaction is initially performed under conditions of low stringency, followed by washes of varying, but higher, stringency. Reference to hybridization stringency relates to such washing conditions.

In accordance with the present invention, "high stringency" conditions can be provided, for example, by hybridization in 50% formamide, 5× Denhardt's solution, 5×SSPE, and 0.2% SDS at 42° C., followed by washing in 0.1×SSPE and 0.1% SDS at 65° C. By comparison, "moderate stringency" can be provided, for example, by hybridization in 50% formamide, 5× Denhardt's solution, 5×SSPE, and 0.2% SDS at 42° C., followed by washing in 0.2×SSPE and 0.2% SDS at 65° C. In addition, "low stringency" conditions can be provided, for example, by hybridization in 10% formamide, 5×Denhardt's solution, 6×SSPE, and 0.2% SDS at 42° C., followed by washing in 1×SSPE and 0.2% SDS at 50° C. It is understood that these conditions may be varied using a variety of buffers and temperatures well known to those skilled in the art.

In a preferred embodiment of the present invention, the nucleic acid is a DNA molecule encoding at least a fragment of the polypeptide of SEQ ID NO:2.

The nucleic acid molecules of the invention, including nucleic acids encoding the N—CBZ-deprotecting enzyme polypeptide of SEQ ID NO:2, can be obtained from mRNA present in *Sphingomonas paucimobilis* cells or other cells to which they are native. It may also be possible to obtain nucleic acid molecules from *Sphingomonas paucimobilis* genomic DNA or the genomic DNA of other organisms. In addition, a nucleic acid encoding a polypeptide can be cloned from either a cDNA or a genomic library in accordance with the protocols described in detail herein.

Nucleic acids of the invention, including nucleic acids encoding the N—CBZ-deprotecting enzyme polypeptide of SEQ ID NO:2, can also be cloned using established polymerase chain reaction (PCR) techniques (see K. Mullis et al., 1986, *Cold Spring Harbor Symp. Quant. Biol.* 51:260; K. H. Roux, 1995, *PCR Methods Appl.* 4:S185) in accordance with the nucleic acid sequence information provided herein. For example, PCR techniques can be used to produce the nucleic acids of the invention, using either RNA (e.g., mRNA) or DNA (e.g., genomic DNA) as templates. Primers used for PCR can be synthesized using the sequence information provided herein and can further be designed to introduce appropriate new restriction sites, if desirable, to facilitate incorporation into a given vector for recombinant expression.

The nucleic acid molecules of the invention, or fragments thereof, can also be chemically synthesized using standard techniques. Various methods of chemically synthesizing polydeoxynucleotides are known, including solid-phase synthesis which, like peptide synthesis, has been fully automated in commercially available DNA synthesizers (see, for example, U.S. Pat. No. 4,598,049 to Itakura et al.; U.S. Pat. No. 4,458,066 to Caruthers et al.; U.S. Pat. Nos. 4,401,796 and 4,373,071 to Itakura).

It will be appreciated by one skilled in the art that variations in one or more nucleotides (up to about 3–4% of the nucleotides) of the nucleic acid molecules encoding a polypeptide may exist among organisms within a population due to natural allelic variation. Any and all such nucleotide variations and resulting amino acid polymorphisms are within the scope of the invention. Furthermore, there may be one or more isoforms or related family members of the polypeptide described herein. Such isoforms or family members are defined as polypeptides that are related in function and amino acid sequence to a N—CBZ-deprotecting enzyme polypeptide of SEQ ID NO:2, but encoded by genes at different loci. Any and all such isoforms and related family members are within the scope of the invention. Also included are related family members from organisms other than *Sphingomonas paucimobilis*. In addition, it is possible to modify the DNA sequence of the N—CBZ-deprotecting enzyme gene using genetic techniques to produce proteins or peptides with altered amino acid sequences.

DNA sequence mutations can be introduced into a nucleic acid encoding a polypeptide by any one of a number of methods, including those for producing simple deletions or insertions, systematic deletions, insertions or substitutions of clusters of bases or substitutions of single bases, to generate desired variants. Mutations of the nucleic acid molecule to generate amino acid substitutions or deletions are preferably obtained by site-directed mutagenesis.

Site directed mutagenesis systems are well known in the art, and can be obtained from commercial sources (see, for example, Amersham-Pharmacia Biotech, Inc., Piscataway, N.J.). Guidance in determining which amino acid residues may be substituted, inserted, or deleted without abolishing biological or immunological activity may be found using computer programs well known in the art, for example, DNASTAR software (DNASTAR, Inc., Madison, Wis.).

Mutant forms of the nucleic acid molecules are considered within the scope of the present invention, where the expressed polypeptide or peptide is capable catalytic or antigenic activity.

A fragment of the nucleic acid molecule encoding a polypeptide is defined as a nucleotide sequence having fewer nucleotides than the nucleotide sequence encoding the entire amino acid sequence of the N—CBZ-deprotecting enzyme polypeptide. In one embodiment of the present invention, a nucleic acid molecule corresponding to a fragment of a nucleic acid sequence can be used as a probe for assaying a biological sample (e.g., cells or cell extracts) for the expression of one or more N—CBZ-deprotecting enzyme nucleic acid sequences, or as a primer for DNA sequencing or PCR amplification. Preferably, such fragments are at least 8, 10, 12, 15, 17, 20, or 21 contiguous nucleotides in length.

In certain embodiments, the nucleic acid molecules of the invention may include linker sequences, modified restriction endonuclease sites, and other sequences useful for molecular cloning, expression, or purification of recombinant protein or fragments thereof. Nucleic acid molecules in accordance with the present invention may also be conjugated with radioisotopes, or chemiluminescent, fluorescent, or other labeling compounds (e.g., digoxigenin). In addition, the nucleic acid molecules of the present invention may be modified by nucleic acid modifying enzymes, for example, kinases or phosphatases. These and other modifications of nucleic acid molecules are well known in the art. In addition, a nucleic acid molecule that encodes a polypeptide, or a functional fragment thereof, can be ligated to a heterologous sequence to encode a fusion protein (also called a chimeric protein) as described in detail herein.

Vectors and Host Cells

Another aspect of the present invention pertains to vectors comprising a nucleic acid of the invention, such as a nucleic acid encoding a N—CBZ-deprotecting enzyme polypeptide or a functional equivalent thereof, as described herein, operably linked to at least one regulatory sequence. "Operably linked" is intended to mean that the nucleotide acid sequence is linked to a regulatory sequence in a manner that allows expression of the nucleotide sequence (i.e., production of mRNA and/or amino acid sequences). Regulatory sequences are known in the art and are selected to direct expression of the desired protein in an appropriate host cell or cell-free expression system. Accordingly, the term regulatory sequence includes promoters, enhancers and other expression control elements (see D. V. Goeddel, 1990, Methods Enzymol. 185:3–7). It should be understood that the design of the expression vector may depend on such factors as the choice of the host cell or expression system to be utilized and/or the type of polypeptide desired to be expressed.

Suitable expression vectors include, but are not limited to, pUC, pBluescript (Stratagene), pET (Novagen, Inc., Madison, Wis.), as well as pREP, pSE420, and pLEX (Invitrogen). Vectors can contain one or more replication and inheritance systems for cloning or expression, one or more markers for selection in the host, e.g. antibiotic resistance, and one or more expression cassettes. The inserted coding sequences can be synthesized by standard methods, isolated from natural sources, or prepared as hybrids. Ligation of the coding sequences to transcriptional regulatory elements (e.g., promoters, enhancers, and/or insulators) and/or to other amino acid encoding sequences can be carried out using established methods. Preferred replication and inheritance systems include M13, ColE1, SV40, baculovirus, lambda, adenovirus, CEN ARS, 2 µm, ARS, and the like. Several regulatory elements (e.g., promoters) have been isolated and shown to be effective in the transcription and translation of heterologous proteins in the various hosts. Such regulatory regions, methods of isolation, manner of manipulation, etc. are known in the art. Non-limiting examples of bacterial promoters include the β-lactamase (penicillinase) promoter; lactose promoter; tryptophan (trp) promoter; araBAD (arabinose) operon promoter; lambda-derived $P_1$ promoter and N gene ribosome binding site; and the hybrid tac promoter derived from sequences of the trp and lac UV5 promoters.

Non-limiting examples of yeast promoters include the 3-phosphoglycerate kinase promoter, glyceraldehyde-3-phosphate dehydrogenase (GAFDH or GAP) promoter, galactokinase (GAL1) promoter, galactoepimerase promoter, and alcohol dehydrogenase (ADH1) promoter. Suitable promoters for mammalian cells include, without limitation, viral promoters, such as those from Simian Virus 40 (SV40), Rous sarcoma virus (RSV), adenovirus (ADV), and bovine papilloma virus (BPV). Alternatively, the endogenous S. paucimobilis regulatory elements (e.g., in SEQ ID NO:3) can be used.

Eukaryotic cells may also require terminator sequences, polyadenylation sequences, and enhancer sequences that modulate gene expression. Sequences that cause amplification of the gene may also be desirable. These sequences are well known in the art. Furthermore, sequences that facilitate secretion of the recombinant product from cells, including, but not limited to, bacteria, yeast, and animal cells, such as secretory signal sequences and/or preprotein or proprotein sequences, may also be included in accordance with established methods. Secretory signal sequences are generally positioned 5' to the nucleotide sequence encoding the protein of interest, although certain signal sequences can be positioned 3' to the nucleotide sequence of interest (see, e.g., Welch et al., U.S. Pat. No. 5,037,743; Holland et al., U.S. Pat. No. 5,143,830). Cell-specific secretory signals can be used with certain cell types (e.g., yeast cells).

Expression and cloning vectors will likely contain a selectable marker, a gene encoding a protein necessary for survival or growth of a host cell transformed with the vector. The presence of this gene ensures growth of only those host cells that express the inserts. Typical selection genes encode proteins that 1) confer resistance to antibiotics or other toxic substances, e.g., ampicillin, neomycin, methotrexate, etc.; 2) complement auxotrophic deficiencies, or 3) supply critical nutrients not available from complex media, e.g., the gene encoding D-alanine racemase for Bacilli. Markers may be an inducible or non-inducible gene and will generally allow for positive selection. Non-limiting examples of markers include the ampicillin resistance marker (i.e., beta-lactamase), tetracycline resistance marker, neomycin/kanamycin resistance marker (i.e., neomycin phosphotransferase), dihydrofolate reductase, glutamine synthetase, and the like. The choice of the proper selectable marker will depend on the host cell, and appropriate markers for different hosts as understood by those of skill in the art.

Suitable cell-free expression systems for use with the present invention include, without limitation, rabbit reticulocyte lysate, wheat germ extract, canine pancreatic microsomal membranes, E. coli S30 extract, and coupled transcription/translation systems (Promega Corp., Madison, Wis.). Suitable host cells include bacteria, fungi, yeast, plant, insect, and animal, mammalian, and human cells.

Specifically included are SF9, C129, 293, NIH 3T3, CHO, COS, HeLa, and *Neurospora* cells. Insect cell systems (i.e., lepidopteran host cells and baculovirus expression vectors) (Luckow and Summers, 1988, *Biotechnology* 6:47–55) are also included.

Preferred host cells include fungal cells, such as *Aspergillus* (*A. niger, A. oryzae*, and *A. fumigatus*), *Fusarium venenatum, Schizosaccharomyces pombe, Saccharomyces cerevisiae, Kluyveromyces lactis, Kluyveromyces fragilis, Ustilago maydis, Candida* (e.g., *C. albicans, C. methylica, C. boidinii, C. tropicalis, C. wickerhamii, C. maltosa*, and *C. glabrata*), *Hansenula* (e.g., *H. anomala, H. polymorpha, H. wingei, H. jadinii* and *H. saturnus*,); and *Pichia* (e.g., *P. angusta, S. paucimobilis, P. anomala, P. stipitis, P. methanolica*, and *P. guilliernondii*) cells. Particularly preferred are bacterial cells, such as *Staphylococcus aureus, Escherichia coli, Bacillus* (e.g., *B. licheniformis, B. amyloliquefaciens*, and *B. subtilis*) and *Streptomyces* (e.g., *Streptomyces lividans* and *Streptomyces coelicolor*) cells.

In general, host cells can be transformed, transfected, or infected as appropriate by any suitable method including electroporation, calcium chloride-, lithium chloride-, lithium acetate/polyethylene glycol-, calcium phosphate-, DEAE-dextran-, liposome-mediated DNA uptake, spheroplasting, injection, microinjection, microprojectile bombardment, phage infection, viral infection, or other established methods. Alternatively, vectors containing the nucleic acids of interest can be transcribed in vitro, and the resulting RNA introduced into the host cell by well-known methods, e.g., by injection (see, Kubo et al., 1988, *FEBS Letts.* 241:119).

Methods for transforming *S. cerevisiae* cells with exogenous DNA and producing recombinant proteins therefrom are found in, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; Murray et al., U.S. Pat. No. 4,845,075, and Kawasaki et al., U.S. Pat. No. 4,931,373). Transformation methods for other yeasts, including *H. polymorpha/P. angusta, S. pombe, K. lactis, K. fragilis, U. maydis, S. paucimobilis, P. methanolica/C. methylica*, and *C. maltosa* are known in the art (see, for example, Gleeson et al., 1986, *J. Gen. Microbiol.* 132: 3459–3465; Cregg, U.S. Pat. No. 4,882,279; and Hiep et al., 1993, *Yeast* 9:1189–1197). *Aspergillus* cells can be transformed according to the methods of McKnight et al., U.S. Pat. No. 4,935,349, while *Acremonium chrysogenum* cells can be transformed in accordance with Sumino et al., U.S. Pat. No. 5,162,228. In general, host cells may integrate the nucleic acid molecules of this invention into chromosomal loci. Alternatively, the host cells may maintain the nucleic acid molecules via episomal vectors.

In one embodiment, an expression vector comprises a nucleic acid encoding at least a fragment of a N—CBZ-deprotecting enzyme polypeptide or functional equivalent thereof. In another embodiment, the expression vector comprises a DNA sequence encoding at least a fragment of a N—CBZ-deprotecting enzyme polypeptide fused in-frame to a DNA sequence encoding a heterologous polypeptide or peptide. Such expression vectors can be used to transfect host cells to thereby produce polypeptides or peptides, including fusion proteins or peptides encoded by nucleic acid molecules as described below.

Several well-established techniques can be used to determine the expression levels and patterns of polypeptides. For example, mRNA levels can be determined utilizing Northern blot analysis (J. C. Alwine et al., 1977, *Proc. Natl. Acad. Sci. USA* 74:5350–5354; I. M. Bird, 1998, *Methods Mol. Biol.* 105:325–36), whereby poly(A)$^+$ RNA is isolated from cells, separated by gel electrophoresis, blotted onto a support surface (e.g., nitrocellulose or Immobilon-Ny+ (Millipore Corp., Bedford, Mass.)), and incubated with a labeled (e.g., fluorescently labeled or radiolabeled) oligonucleotide probe that is capable of hybridizing with the mRNA of interest.

Alternatively, mRNA levels can be determined by quantitative (for review, see W. M. Freeman et al., 1999, *Biotechniques* 26:112–122) or semi-quantitative RT-PCR analysis (Ren et al., *Mol. Brain Res.* 59:256–63). In accordance with this technique, poly(A)$^+$ RNA is isolated from cells, used for cDNA synthesis, and the resultant cDNA is incubated with PCR primers that are capable of hybridizing with the template and amplifying the template sequence to produce levels of the PCR product that are proportional to the cellular levels of the mRNA of interest. Another technique, in situ hybridization, can also be used to determine mRNA levels (reviewed by A. K. Raap, 1998, *Mutat. Res.* 400: 287–298). In situ hybridization techniques allow the visual detection of mRNA in a cell by incubating the cell with a labeled (e.g., fluorescently labeled or digoxigenin labeled) oligonucleotide probe that hybridizes to the mRNA of interest, and then examining the cell by microscopy.

N—CBZ-deprotecting enzyme polypeptides, fragments, modifications, or variants can be also be assessed directly by well-established techniques. For example, host cell expression of the recombinant polypeptides can be evaluated by western blot analysis using antibodies specifically reactive with these polypeptides (see above). Production of secreted forms of the polypeptides can be evaluated by immunoprecipitation using monoclonal antibodies that are specifically reactive the polypeptides. Other, more preferred, assays take advantage of the functional characteristics of the polypeptides. As previously set forth, N—CBZ-deprotecting enzyme polypeptides can be used in various reactions to deprotect carbobenzyloxy (CBZ)-protected amines and alcohols. Thus, the N—CBZ-deprotecting enzyme polypeptide function can be assessed by measuring the products of these reactions requiring co-factor regeneration. In specific aspects, any one of the assays described herein can be employed.

Polypeptides

A further aspect of the present invention pertains to N—CBZ-deprotecting enzyme polypeptides, and variants, modifications, and fragments thereof. An N—CBZ-deprotecting enzyme polypeptide comprises or consists of the amino acid sequence of SEQ ID NO:2, or comprises or consists of the amino acid sequence encoded by the nucleotide sequence deposited as ATCC Accession Number PTA-5051. Preferred variants, modifications and fragments of the N—CBZ-deprotecting enzyme polypeptide are functional equivalents of the N—CBZ-deprotecting enzyme polypeptide of SEQ ID NO:2. The present invention encompasses isolated N—CBZ-deprotecting enzyme polypeptide, and variants, modifications, and fragments thereof. The present invention also encompasses recombinant (including isolated and non-isolated) N—CBZ-deprotecting enzyme polypeptide, and variants, modifications, and fragments thereof. Polypeptide fragments (i.e., peptides) can range in size from 5 amino acid residues to all but one residue of the entire amino acid sequence. Thus, a peptide can be at least 5, 15, 20, 25, 30, 50, 100, 150, 200, 250, 300, 350, 400, 405, 410, 415, 417, 419, 421, 423, 425 or more consecutive amino acid residues of a N—CBZ-deprotecting enzyme polypeptide, such as SEQ ID NO:2. Preferred are polypeptides that share moderate homology with the N—CBZ-deprotecting enzyme polypeptide of SEQ ID NO:2. More preferred are polypeptides that share substantial homology with the polypeptide.

The term "functional equivalent" is intended to include proteins which differ in amino acid sequence from the N—CBZ-deprotecting enzyme polypeptide of SEQ ID NO:2, but which perform at least one characteristic function of the polypeptide, such catalytic or antigenic activity. For example, a functional equivalent of a polypeptide may have a modification such as a substitution, addition or deletion of an amino acid residue which is not directly involved in the function of this polypeptide. Various modifications of the polypeptide to produce functional equivalents of these polypeptides are described in detail herein. A preferred functional equivalent is capable of deprotecting an N—CBZ-protected amino acid, where the conversion rate is preferably at least 10%, 20%, 30%, 40%, 50%, 60%, 70%, 80%, 85%, 90%, 95%, 99% or 100%. Preferably the N—CBZ-protected amino acid is an N—CBZ-protected L-amino acid, more preferably N—CBZ-L-phenylalanine, and the conversion rate is preferably at least 80%, 85%, 90%, 95%, 99%, or 100%. Exemplary deprotection assays are given the Examples herein, such as in Examples 4, 5, and 13. Additionally, deprotection can be assayed by the following assay.

An N—CBZ-protected D- or L-amino acid is incubated with an enzyme source at 28 to 45 degrees C. for 24 to 72 hours. The reaction is stopped by addition of 2 volumes of 50% acetonitrile. The samples are filtered and analyzed by HPLC.

It is also possible to modify the structure of a polypeptide of the invention, such as a N—CBZ-deprotecting enzyme polypeptide, for such purposes as increasing solubility, enhancing reactivity, or increasing stability (e.g., shelf life ex vivo and resistance to proteolytic degradation in vivo). Such modified proteins are considered functional equivalents of the N—CBZ-deprotecting enzyme polypeptide as defined herein. Preferably, polypeptides are modified so that they retain catalytic activity. Those residues shown to be essential for activity can be modified by replacing the essential amino acid with another, preferably similar amino acid residue (a conservative substitution) whose presence is shown to enhance, diminish, but not eliminate, or not effect receptor interaction. In addition, those amino acid residues that are not essential for catalysis can be modified by being replaced by another amino acid whose incorporation may enhance, diminish, or not effect reactivity.

In order to enhance stability and/or reactivity, a N—CBZ-deprotecting enzyme polypeptide can be altered to incorporate one or more polymorphisms in the amino acid sequence. Additionally, D-amino acids, non-natural amino acids, or non-amino acid analogs can be substituted or added to produce a modified polypeptide. Furthermore, the polypeptides disclosed herein can be modified using polyethylene glycol (PEG) according to known methods (S. I. Wie et al., 1981, *Int. Arch. Allergy Appl. Immunol.* 64(1):84–99) to produce a protein conjugated with PEG. In addition, PEG can be added during chemical synthesis of the protein. Other possible modifications include phosphorylation, sulfation, reduction/alkylation (Tarr, 1986, *Methods of Protein Microcharacterization*, J. E. Silver, Ed., Humana Press, Clifton, N.J., pp. 155–194); acylation (Tarr, supra); chemical coupling (Mishell and Shiigi (Eds.), 1980, *Selected Methods in Cellular Immunology*, W H Freeman, San Francisco, Calif.; U.S. Pat. No. 4,939,239); and mild formalin treatment (Marsh, 1971, *Int. Arch. of Allergy and Appl. Immunol.* 41:199–215).

Modified polypeptides can have conservative changes, wherein a substituted amino acid has similar structural or chemical properties, e.g., replacement of leucine with isoleucine. More infrequently, a modified polypeptide can have non-conservative changes, e.g., substitution of a glycine with a tryptophan. Guidance in determining which amino acid residues can be substituted, inserted, or deleted without abolishing biological or immunological activity can be found using computer programs well known in the art, for example, DNASTAR software (DNASTAR, Inc., Madison, Wis.)

As non-limiting examples, conservative substitutions in amino acid sequence can be made in accordance with the following table:

| Original Residue | Conservative Substitution(s) | Original Residue | Conservative Substitution(s) |
|---|---|---|---|
| Ala | Ser | Leu | Ile, Val |
| Arg | Lys | Lys | Arg, Gln, Glu |
| Asn | Gln, His | Met | Leu, Ile |
| Asp | Glu | Phe | Met, Leu, Tyr |
| Cys | Ser | Ser | Thr |
| Gln | Asn | Thr | Ser |
| Glu | Asp | Trp | Tyr |
| Gly | Pro | Tyr | Trp, Phe |
| His | Asn, Gln | Val | Ile, Leu |
| Ile | Leu, Val | | |

Substantial changes in function or immunogenicity can be made by selecting substitutions that are less conservative than those shown in the table, above. For example, non-conservative substitutions can be made which more significantly affect the structure of the polypeptide in the area of the alteration, for example, the alpha-helical, or beta-sheet structure; the charge or hydrophobicity of the molecule at the target site; or the bulk of the side chain. The substitutions which generally are expected to produce the greatest changes in the polypeptide's properties are those where 1) a hydrophilic residue, e.g., seryl or threonyl, is substituted for (or by) a hydrophobic residue, e.g., leucyl, isoleucyl, phenylalanyl, valyl, or alanyl; 2) a cysteine or proline is substituted for (or by) any other residue; 3) a residue having an electropositive side chain, e.g., lysyl, arginyl, or histidyl, is substituted for (or by) an electronegative residue, e.g., glutamyl or aspartyl; or 4) a residue having a bulky side chain, e.g., phenylalanine, is substituted for (or by) a residue that does not have a side chain, e.g., glycine.

Preferred polypeptide embodiments further include an isolated polypeptide comprising an amino acid sequence sharing at least 45, 50, 60, 70, 75, 80, 85, 86, 90, 95, 97, 98, 99, 99.5 or 100% identity with the amino acid sequence of SEQ ID NO:2. This polypeptide sequence may be identical to the sequence of SEQ ID NO:2, or may include up to a certain integer number of amino acid alterations as compared to the reference sequence.

Percent sequence identity can be calculated using computer programs or direct sequence comparison. Preferred computer program methods to determine identity between two sequences include, but are not limited to, the GCG program package, FASTA, BLASTP, and TBLASTN (see, e.g., D. W. Mount, 2001, *Bioinformatics: Sequence and Genome Analysis*, Cold Spring Harbor Laboratory Press, Cold Spring Harbor, N.Y.). The BLASTP and TBLASTN programs are publicly available from NCBI and other sources. The well-known Smith Waterman algorithm may also be used to determine identity.

Exemplary parameters for amino acid sequence comparison include the following: 1) algorithm from Needleman and Wunsch, 1970, *J. Mol. Biol.* 48:443–453; 2) BLOSSUM62 comparison matrix from Hentikoff and Hentikoff, 1992, *Proc. Natl. Acad. Sci. USA* 89:10915–10919; 3) gap penalty=12; and 4) gap length penalty=4. A program useful with these parameters is publicly available as the "gap" program (Genetics Computer Group, Madison, Wis.). The aforementioned parameters are the default parameters for polypeptide comparisons (with no penalty for end gaps). Alternatively, polypeptide sequence identity can be calculated using the following equation: % identity=(the number of identical residues)/(alignment length in amino acid residues)*100. For this calculation, alignment length includes internal gaps but does not include terminal gaps.

In accordance with the present invention, polypeptides may be identical to the sequence of SEQ ID NO:2, or may include up to a certain integer number of amino acid alterations. Polypeptide alterations are selected from the group consisting of at least one amino acid deletion, substitution, including conservative and non-conservative substitution, or insertion. Alterations may occur at the amino- or carboxy-terminal positions of the reference polypeptide sequence or anywhere between those terminal positions, interspersed either individually among the amino acids in the reference sequence or in one or more contiguous groups within the reference sequence. In specific embodiments, polypeptide variants may be encoded by nucleic acids comprising single nucleotide polymorphisms and/or alternate splice variants.

N—CBZ-deprotecting enzyme polypeptides may also be modified by conjugation with a label capable of providing a detectable signal, either directly or indirectly, including, for example, radioisotopes and fluorescent compounds. Non-limiting examples of fluorescent compounds include Cy3, Cy5, GFP (e.g., EGFP, DsRed, dEFP, etc. (CLONTECH, Palo Alto, Calif.)), Alexa, BODIPY, fluorescein (e.g., FluorX, DTAF, and FITC), rhodamine (e.g., TRITC), auramine, Texas Red, AMCA blue, and Lucifer Yellow. Suitable isotopes include, but are not limited to, $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

The invention also relates to isolated, synthesized and/or recombinant portions or fragments of a N—CBZ-deprotecting enzyme polypeptide, such as SEQ ID NO:2, as described herein. Polypeptide fragments (i.e., peptides) can be made which have full or partial function on their own, or which when mixed together (though fully, partially, or nonfunctional alone), spontaneously assemble with one or more other polypeptides to reconstitute a functional protein having at least one functional characteristic of a protein of this invention. In addition, polypeptide fragments may comprise, for example, one or more domains of the polypeptide (e.g., catalytic domain) disclosed herein. Specifically, the catalytic domain of can be used to study the structure/function of the enzyme.

The polypeptides of the present invention may be isolated from wild-type or mutant *S. paucimobilis* cells or other cells in which they are native, from heterologous organisms or cells (e.g., bacteria, yeast, insect, plant, or mammalian cells) comprising recombinant polypeptides of the invention, or from cell-free translation systems (e.g., wheat germ, microsomal membrane, or bacterial extracts) in which a polypeptide of the invention, such as a N—CBZ-deprotecting enzyme polypeptide, is expressed. Furthermore, the polypeptides may be part of recombinant fusion proteins.

The polypeptides can also, advantageously, be made by synthetic chemistry. Polypeptides may be chemically synthesized by commercially available automated procedures, including, without limitation, exclusive solid phase synthesis, partial solid phase methods, fragment condensation or classical solution synthesis.

Isolation and Production of Polypeptides

Yet another aspect of the present invention pertains to methods of isolating N—CBZ-deprotecting enzyme polypeptides, or variants, modifications, or fragments thereof from biological samples (e.g., cells, cell extracts or lysates, cell membranes, growth media, etc.). Fragments of N—CBZ-deprotecting enzyme polypeptides (i.e., peptides) include portions, preferably, having the same or equivalent function or activity as the full-length polypeptide. Naturally occurring, synthetic, and recombinant forms of the polypeptides or peptides may be used in the methods according to the present invention. Methods for directly isolating and purifying polypeptides or peptides from cellular or extracellular lysates are well known in the art (see E. L. V. Harris and S. Angal (Eds.), 1989, *Protein Purification Methods: A Practical Approach*, IRL Press, Oxford, England). Such methods include, without limitation, preparative disc-gel electrophoresis, isoelectric focusing, high-performance liquid chromatography (HPLC), reversed-phase HPLC, gel filtration, ion exchange and partition chromatography, and countercurrent distribution, and combinations thereof. Methods of isolating polypeptides are further elucidated in the Examples.

In addition, antibody-based methods can be used to isolate natural, synthetic, or recombinantly produced polypeptides or peptides of the invention. Antibodies that recognize these polypeptides, or peptides derived therefrom, can be produced and isolated using methods known and practiced in the art (see below). Polypeptides or peptides can then be purified from a crude lysate by chromatography on antibody-conjugated solid-phase matrices (see E. Harlow and D. Lane, 1999, *Using Antibodies: A Laboratory Manual*, Cold Spring Harbor Laboratory, Cold Spring Harbor, N.Y.). Other isolation methods known and used in the art may also be employed.

Yet another aspect of the present invention pertains to methods of producing recombinant polypeptides or peptides. DNA sequences encoding the polypeptides or peptides can be cloned into a suitable vector for expression in intact host cells or in cell-free translation systems as described above (see also J. Sambrook et al., 1989, *Molecular Cloning: A Laboratory Manual*, 2d Ed., Cold Spring Harbor Laboratory Press, Cold Spring Harbor, N.Y.). DNA sequences can be optimized, if desired, for more efficient expression in a given host organism. For example, codons can be altered to conform to the preferred codon usage in a given host cell or cell-free translation system using techniques routinely practiced in the art. After culturing the host cell under suitable conditions, or subjecting the cell-free translation system to suitable conditions, recombinant polypeptide is recovered.

For some purposes, it may be preferable to produce peptides or polypeptides in a recombinant system wherein the peptides or polypeptides carry additional sequence tags to facilitate purification. Such markers include epitope tags and protein tags. Non-limiting examples of epitope tags include c-myc, haemagglutinin (HA), polyhistidine (6X-HIS), GLU—GLU, and DYKDDDDK (FLAG®) epitope tags. Non-limiting examples of protein tags include glutathione-S-transferase (GST), green fluorescent protein (GFP), and maltose binding protein (MBP).

Epitope and protein tags can be added to peptides by a number of established methods. For example, DNA sequences encoding epitope tags can be inserted into protein-coding sequences as oligonucleotides or as primers used in PCR amplification. As an alternative, protein-coding sequences can be cloned into specific vectors that create fusions with epitope tags; for example, pRSET vectors (Invitrogen Corp., San Diego, Calif.). Similarly, protein tags can be added by cloning the coding sequence of a polypeptide or peptide into a vector that creates a fusion between the polypeptide or peptide and a protein tag of interest. Suitable vectors include, without limitation, the exemplary plasmids, pGEX (Amersham-Pharmacia Biotech, Inc., Piscataway, N.J.), pEGFP (CLONTECH Laboratories, Inc., Palo Alto, Calif.), and pMAL™ (New England BioLabs, Inc., Beverly, Mass.). Following expression, the epitope or protein tagged polypeptide or peptide can be purified from a crude lysate of the translation system or host cell by chromatography on an appropriate solid-phase matrix. In some cases, it may be preferable to remove the epitope or protein tag (i.e., via protease cleavage) following purification.

In various embodiments, the recombinant polypeptides are secreted to the cell surface, retained in the cytoplasm of the host cells, or secreted into the growth media. In each case, the production of polypeptides can be established using anti-N—CBZ-deprotecting enzyme antibodies, or catalytic assays. The cell-surface and cytoplasmic recombinant polypeptides can be isolated following cell lysis and extraction of cellular proteins, while the secreted recombinant polypeptides can be isolated from the cell growth media by standard techniques (see I. M. Rosenberg (Ed.), 1996, *Protein Analysis and Purification: Benchtop Techniques*, Birkhauser, Boston, Cambridge, Mass.).

Methods to improve polypeptide production may include 1) the use of bacterial expressed fusion proteins comprising signal peptides or targeting sequences to promote secretion (Tessier et al., 1991, *Gene* 98:177–83; Garnier et al., 1995, *Biotechnology* 13:1101–4); 2) the use of serum-free and protein-free culture systems for economical polypeptide production (Zang et al., 1995, *Biotechnology* 13:389–92); 3) the use of the eukaryotic regulated secretory pathway for increased production and harvesting efficiency (see Chen et al., 1995, *Biotechnology* 13:1191–97). Polypeptide production may also be optimized by the utilization of a specific vector, host cell, expression system, or production protocol, as described in detail herein.

Large-scale microbial protein production can be achieved using well-established methods (see, e.g., W. Crueger and A. Crueger, 1990, *Biotechnology: A Textbook of Industrial Microbiology* Sinauer Associates, Sunderland, Mass.; A. N. Glazer and H. Nikaido, 1995, *Microbial biotechnology: fundamentals of applied microbiology* Freeman, New York, N.Y.; C. M. Brown et al., 1987, *Introduction to Biotechnology: Basic Microbiology*, Vol. 10, Blackwell, Oxford, UK). Methods for scaling-up baculovirus protein production can be found, for example, in R. L. Tom et al., 1995, *Methods Mol. Biol.* 39:203–24; R. L. Tom et al., 1995, *Appl. Microbiol. Biotechnol.* 44:53–8; S. A. Weiss, et al., 1995, *Methods Mol. Biol.* 39:79–95; and C. D. Richardson (Ed.), 1995, *Baculovirus Expression Protocols: Methods in Molecular Biology*, Vol. 39, Humana Press, Totowa, N. J. In additional, large-scale protein production services are commercially available from, e.g., Pan Vera Corp., Madison, Wis.; Oxford Expression Technologies, Oxford UK; BioXpress Laboratory, Athens, Ga.; and Recombinant Protein Expression Laboratory, Gainesville, Fla.

In general, large-scale microbial enzyme production systems employ the following procedures. Screens are used to test enzyme activity, pH optimum, temperature optimum, secretion (downstream processing), and the ability to grow the organism in inexpensive large-scale fermentation systems (high population densities from inexpensive carbon and nitrogen feedstocks, e.g., corn syrup, molasses, soybean meal, gluten, etc.). Strain improvements are created by random mutagenesis and screening or directed genetic manipulation (e.g., in *Bacillus, Streptomyces, Aspergillus* and *Saccharonmyces* strains). For example, mutant strains can provide 1) relief of repression (e.g., catabolite repression); 2) increased promoter strength; 3) higher affinity ribosome-binding sites; 4) higher efficiency of mRNA leader translation; 5) increased mRNA half life; 6) increased translation efficiency through altered codon usage; 7) improvement of secretion efficiency; and 8) increased gene dosage (i.e., via chromosomal amplification or plasmid amplification). Process improvements are implemented by screening feeding strategies (e.g., batch, fed-batch, continuous, or recycle), reactor configurations, stirring methods (e.g., via impeller, bubble, air lift, packed bed, solid state, or hollow fiber), pH control, foam, and temperature. Enzymes produced by exemplary large-scale microbial systems include various serine proteinases, Zn metalloproteinases, aspartic proteinases, isomerases, pectinases, lipases, α-amylase, cellases, and glucomylases.

Uses for Polypeptides

The N—CBZ-deprotecting enzyme polypeptides, and fragments, modifications and variants thereof, may be used in any of the following methods.

One aspect of the present invention provides a method of deprotecting an amine or alcohol protected with a carbobenzyloxy-protecting group of the formula

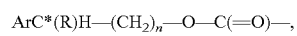

where the substituents are described as follows, the method comprising: contacting the protected amine or alcohol with an enzyme effective to remove the protecting group; and recovering the amine or alcohol. R is H or independently the same as Ar, and n is 0 or 1–4. Ar refers to an aromatic or heteroaromatic ring with 5 to 6 ring atoms and one to two heteroatoms selected from O, N or S. Ar may be substituted with amino, alkanoyloxy, alkoxy, alkyl, alkylamino, allyl, carboxy, cycloalkyl, halo, haloalkyl, hydroxy, hydroxyalkyl or nitro, or up to one group which is (a) Ar* which is independently the same as Ar except that it is not substituted with a further aryl, (b) Ar*-alkyl or (c) Ar*O—. A ring atom of Ar adjacent to C* can be substituted with —CH$_2$—, —O—, —NH—, —S(O)$_q$— or —P(O)$_r$—, to form a bridge to a corresponding position on R when R is Ar, wherein q is 0 or 1–2 and r is 0 or 1–2. In one embodiment, n is 0 when R is H. In another embodiment, n is 1 where R is the same as Ar. As illustrated by the Examples (see Table 2), the method is stereospecific, and thus can be used for resolving racemic mixtures.

These protecting groups are illustrated by such compounds as 9-fluorenylmethyl carbamate, 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)methyl carbamate, benzyl carbamate, p-methoxybenzyl carbamate, p-nitrobenzyl carbamate, p-bromobenzyl carbamate, p-chlorobenzyl carbamate, 2,4-dichlorobenzyl carbamate, 9-anthrylmethyl carbamate, diphenyl methyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate, m-nitrobenzyl carbamate, 3,5-dimethoxybenzyl carbamate, 3,4-dimethoxy-6-nitrobenzyl carbamate, S-benzyl thiocarbamate, p-cyanobenzyl carbamate, 2-furanylmethyl carbamate, 4-(trimethylammonium) benzyl carbamate and 2,4,6-trimethylbenzyl carbamate. Protecting groups such as these are described in standard texts such as Greene and Wuts, *Protective Groups in Organic Synthesis*, John Wiley & Sons, New York, 1991 (especially pp. 315–348).

Alkyl components of substitutions are $C_1$–$C_6$ or $C_2$–$C_6$ where a $C_1$ moiety is chemically inappropriate (e.g., for alkanoyl). Cycloalkyl radicals are $C_3$–$C_6$. Haloalkyl preferably refers to perhaloalkyl, and preferably trifluoromethyl. Halo is preferably chloro or fluoro.

In one embodiment, the protecting group is a phenylmethyloxycarbonyl group, where the phenyl can be substituted. Illustrated substitutions to the phenylmethyloxycarbonyl include, for example, those recited above for Ar.

A source of the enzyme used in the invention can be isolated as an isolated bacteria having the appropriate activity. The method of isolation is preferably selection by growth on a medium in which sufficient growth-supporting nitrogen can only be obtained from an amine compound in which the amine is protected by the carbamate protecting group in question, or related carbamate protecting group. The examples below illustrate that such bacteria can be isolated from very ordinary sources of bacteria, such as environmental or soil samples.

The examples below exemplify that the selection technique identified by the inventors is effective to isolate appropriate bacteria, and thereby an appropriate enzyme source, using ordinary experimentation. The examples are for bacteria isolated by selecting for growth with a nitrogen source that is CBZ-protected. However, this illustration confirms Applicants' understanding that appropriate enzymes can be collected without undue experimentation using the same approach with the protecting group matched to the protecting group sought to be removed.

Where the amine or alcohol involved in the enzymatic removal is identified as the most likely candidate for a cause of a proposed substrate being resistant to cleavage by a given enzyme, an appropriately protected version of that amine (or an analog, or an amine analog of the alcohol) can be used to select another bacteria, and hence another enzyme. A collection of separate deprotecting enzymes or bacterial cultures each producing a useful enzyme can be stored and screened in the event that substitute enzymes are needed. Where the amine or alcohol to be protected and deprotected is a complex molecule, with the amine or alcohol portion linked to relatively distant moieties, then the amine or alcohol model used in the selection process can be modeled on the portion of the complex adjacent to the amine or alcohol. Preferably care is taken so that nearby moieties that in the complex molecule are derivatized are analogously derivatized.

As illustrated below, bacterial whole cells, extracts from whole cells, or purified enzyme preparations can be used to effect the deprotection provided by the invention. The enzyme acts catalytically so that small amounts are typically used, and as the impurities provided by enzyme sources (e.g., those of lesser purity) should not produce notable quantities of material that should behave like the intended product. Thus, impurities provided by the enzyme source are quickly selected against in post-reaction workup. In particular, where extracts are used, the impurities are by and large macromolecules; and since the typical intended products are typically not macromolecules, the impurities are quickly segregated away from the product.

Also as illustrated below, the substrate used in the enzyme selection process provides a facile tool for measuring enzyme activity, and hence for isolating the enzyme with selective microbiological enrichment and traditional protein chemistry techniques.

The amino or hydroxyl group protected by the protecting group can be any amine alcohol on any molecule. In many embodiments, the amine or alcohol is found on a molecule that is of a size amenable to non-repetitive synthetic techniques. (Of course, the deprotection technique of the invention can also be used in repetitive techniques such as are used in peptide or nucleic acid synthesis.) In one preferred embodiment, the amine or alcohol is part of a bioactive agent that is bioavailable to an animal after oral ingestion, or is part of a precursor to such a bioactive agent.

In one aspect, the amine is preferably an α- or β-amino acid, more preferably an α-amino acid.

The amine can be, for example, alanine, valine, leucine, isoleucine, proline, 4-hydroxyproline, phenylalanine, tryptophan, methionine, glycine, serine, homoserine, threonine, cysteine, homocysteine, tyrosine, asparagine, glutamine, aspartic acid, glutamic acid, lysine, α-amino-ε-caprolactam (lysine lactam), α-amino-δ,δ-dimethyl-ε-caprolactam, ε-methyllysine, ornithine, arginine, histidine or 3-methyhistidine, or any of the foregoing substituted on an alkyl portion thereof with hydroxy or alkyl, on an amino with up to one alkyl, or on a phenyl moiety substituted with the radicals recited above for Ar. Such an amino acid can be an L or D amino acid, preferably an L-amino acid. Moreover, such amino acid can be derivatized to form a portion of a larger molecule via bonds formed by dehydration reactions with amine or carboxylic acid moieties, or by carbon-nitrogen bonds formed at the amine moieties.

Another class of alpha amino acids particularly useful in the invention are according to the following formula:

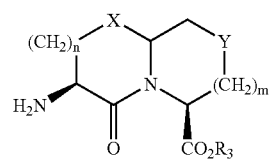

wherein: m is zero or one; Y is $CH_2$, S—(O)$_t$ or O provided that Y is S—(O)$_t$ or O only when m is one; X is S—(O)$_t$ or O; n is one or two; t is 0, 1 or 2; $R_3$ is hydrogen, alkyl, substituted alkyl, aryl-(CH$_2$)$_p$—; and p is 0 or 1–6. Of these amines, the following is a particularly preferred amine:

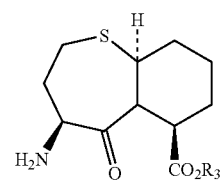

These compounds are described in more detail in U.S. Pat. No. 5,508,272. The teachings therein on making and using these compounds is incorporated by reference. Additional compounds of specific interest with respect to the use of this invention are described in WO 00/47207 and U.S. Pat. No. 5,552,397. The teachings on making and using the compounds described therein are incorporated by reference.

Protected amines or alcohols are typically formed from reacting

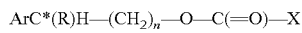

with the corresponding amines or hydroxides, where X is a leaving group (e.g., bromo, chloro, tosyl). The ArC*(R)H—(CH$_2$)$_n$—O—C(=O)—X is for example formed by reacting ArC*(R)H—(CH$_2$)$_n$—OH with phosgene, carbomyl diaidazole, triphosgene or a comparable reagents.

In a preferred embodiment of the above-described method of deprotecting a amine or alcohol, the enzyme effective to remove the protecting group is an N—CBZ-deprotecting enzyme polypeptide, or fragment, modification or variant thereof, of the present invention. More preferably the N—CBZ-deprotecting enzyme polypeptide, or fragment, modification or variant thereof, is isolated or recombinant. More preferably, the isolated or recombinant polypeptide has the amino acid sequence of SEQ ID NO:2.

Another aspect of the present invention provides a method of isolating a bacteria producing an enzyme effective to remove a protecting group comprising: growing prospective bacteria on a medium having a growth selective amount of an amine compound that is protected as above; and isolating bacteria that grow on said medium.

Another aspect of the present invention provides a method of resolving a racemic mixture of a compound having a amino or hydroxyl moiety that is directly bonded to a chiral carbon comprising: providing a derivative of the compound in which the amine or alcohol is protected with a group of formula ArC*(R)H—(CH$_2$)$_n$—O—C(=O)—, wherein the substituents are as described above, comprising: contacting the protected compound with an enzyme effective to remove the protecting group; and isolating the compound or protected derivative thereof in a composition that is enantiomerically enriched in the desired enantioner. In this method, the amine or alcohol protected with such a group is stereospecifically hydrolyzed with the method of the invention. The desired enantiomer is either that hydrolyzed or that resistant to hydrolysis.

In one embodiment of the method of resolving a racemic mixture, the contacting step effectuates the following reaction:

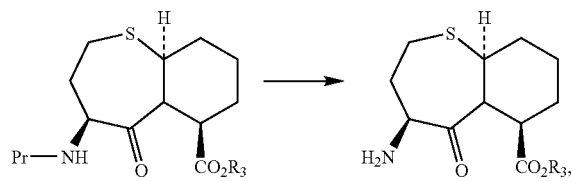

where Pr— is the above-described protecting group. In another embodiment, the contacting effectuates the following reaction:

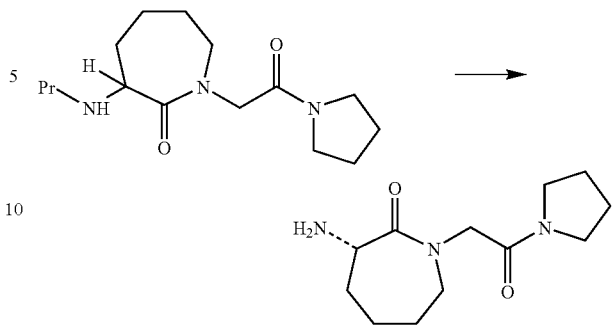

In yet another embodiment, the contacting effectuates the following reaction:

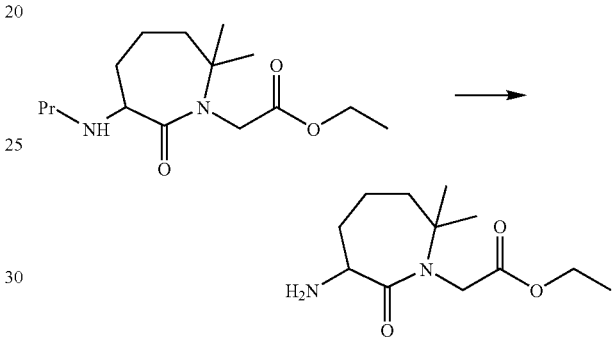

In a preferred embodiment of the above-described method of resolving a racemic mixture, the enzyme effective to remove the protecting group is an N—CBZ-deprotecting enzyme polypeptide, or fragment, modification or variant thereof, of the present invention. More preferably the N—CBZ-deprotecting enzyme polypeptide, or fragment, modification or variant thereof, is isolated or recombinant. More preferably, the isolated or recombinant polypeptide has the amino acid sequence of SEQ ID NO:2.

Additional objects and advantages afforded by the present invention will be apparent from the detailed description and exemplification hereinbelow.

For use in medical or industrial applications, N—CBZ-deprotecting enzyme polypeptides, peptides, modifications, or variants thereof can be added to a particular chemical reaction by any available means. For example, polypeptides isolated from natural (e.g., *S. paucimobilis* cells), recombinant, or synthetic sources may be used. Alternatively, cell extracts or whole cells expressing a secreted form of may be used. Different sources of can be compared to determine the source that results in, for example, the highest yields of product or the lowest production costs. Notably, recombinant production of is expected to have lower production costs and time requirements than required for the purification of the native enzyme.

Antibodies

Another aspect of the invention pertains to antibodies directed to N—CBZ-deprotecting enzyme polypeptides, or fragments or variants thereof. The invention provides polyclonal and monoclonal antibodies that bind polypeptides or peptides. The antibodies may be elicited in an animal host (e.g., non-human mammal) by immunization with enzyme components. Antibodies may also be elicited by in vitro immunization (sensitization) of immune cells. The immunogenic components used to elicit the production of antibodies may be isolated from cells or chemically synthesized. The antibodies may also be produced in recombinant systems programmed with appropriate antibody-encoding DNA. Alternatively, the antibodies may be constructed by biochemical reconstitution of purified heavy and light chains. The antibodies include hybrid antibodies, chimeric antibodies, and univalent antibodies. Also included are Fab fragments, including $Fab_1$ and $Fab(ab)_2$ fragments of antibodies.

In accordance with the present invention, antibodies are directed to a N—CBZ-deprotecting enzyme polypeptide of SEQ ID NO:2, or variants, or portions thereof. For example, antibodies can be produced to bind to a polypeptide encoded by an alternate splice variant or SNP variant of SEQ ID NO:1. An isolated N—CBZ-deprotecting enzyme polypeptide of SEQ ID NO:2, or variant, or portion thereof, can be used as an immunogen to generate antibodies using standard techniques for polyclonal and monoclonal antibody preparation. A full-length polypeptide can be used or, alternatively, the invention provides antigenic peptide portions of the polypeptide for use as immunogens. An antigenic peptide comprises at least 5 contiguous amino acid residues, preferably at least 10, 20, 30, 40, 50, 100, 150, 200, 250, 300, 350, or 400 contiguous amino acid residues, of the amino acid sequence shown in SEQ ID NO:2, or a variant thereof, and encompasses an epitope of a polypeptide such that an antibody raised against the peptide forms a specific immune complex with a amino acid sequence.

An appropriate immunogenic preparation can contain, for example, recombinantly produced polypeptide or a chemically synthesized polypeptide, or portions thereof. The preparation can further include an adjuvant, such as Freund's complete or incomplete adjuvant, or similar immunostimulatory agent. A number of adjuvants are known and used by those skilled in the art. Non-limiting examples of suitable adjuvants include incomplete Freund's adjuvant, mineral gels such as alum, aluminum phosphate, aluminum hydroxide, aluminum silica, and surface-active substances such as lysolecithin, pluronic polyols, polyanions, peptides, oil emulsions, keyhole limpet hemocyanin, and dinitrophenol. Further examples of adjuvants include N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-Lalanyl-D-isoglutaminyl-L-alanine-2-(1'-2'-dipalmitoyl-sn-glycero-3 hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. A particularly useful adjuvant comprises 5% (wt/vol) squalene, 2.5% Pluronic L121 polymer and 0.2% polysorbate in phosphate buffered saline (Kwak et al., 1992, New Eng. J. Med. 327:1209–1215). Preferred adjuvants include complete BCG, Detox, (RIBI, Immunochem Research Inc.), ISCOMS, and aluminum hydroxide adjuvant (Superphos, Biosector). The effectiveness of an adjuvant may be determined by measuring the amount of antibodies directed against the immunogenic peptide.

Polyclonal antibodies to polypeptides can be prepared as described above by immunizing a suitable subject (e.g., horse, donkey, goat, rabbit, rat, mouse, chicken, or other non-human animal) with a immunogen. The antibody titer in the immunized subject can be monitored over time by standard techniques, such as with an enzyme linked immunosorbent assay (ELISA) using immobilized polypeptide or peptide. If desired, the antibody molecules can be isolated from the mammal (e.g., from the blood) and further purified by well-known techniques, such as protein A chromatography to obtain the IgG fraction.

At an appropriate time after immunization, e.g., when the antibody titers are highest, antibody-producing cells can be obtained from the subject and used to prepare monoclonal antibodies by standard techniques, such as the hybridoma technique (see Kohler and Milstein, 1975, Nature 256: 495–497; Brown et al., 1981, J. Immunol. 127:539–46; Brown et al., 1980, J. Biol. Chem. 255:4980–83; Yeh et al., 1976, PNAS 76:2927–31; and Yeh et al., 1982, Int. J. Cancer 29:269–75), the human B cell hybridoma technique (Kozbor et al., 1983, Immunol. Today 4:72), the EBV-hybridoma technique (Cole et al., 1985, Monoclonal Antibodies and Cancer Therapy, Alan R. Liss, Inc., pp. 77–96) or trioma techniques.

The technology for producing hybridomas is well-known (see generally R. H. Kenneth, 1980, Monoclonal Antibodies: A New Dimension In Biological Analyses, Plenum Publishing Corp., New York, N.Y.; E. A. Lerner, 1981, Yale J. Biol. Med., 54:387–402; M. L. Gefter et al., 1977, Somatic Cell Genet. 3:231–36). In general, an immortal cell line (typically a myeloma) is fused to lymphocytes (typically splenocytes) from a mammal immunized with a immunogen as described above, and the culture supernatants of the resulting hybridoma cells are screened to identify a hybridoma producing a monoclonal antibody that binds polypeptides or peptides.

Any of the many well known protocols used for fusing lymphocytes and immortalized cell lines can be applied for the purpose of generating an monoclonal antibody to a polypeptide (see, e.g., G. Galfre et al., 1977, Nature 266: 55052; Gefter et al., 1977; Lerner, 1981; Kenneth, 1980). Moreover, the ordinarily skilled worker will appreciate that there are many variations of such methods. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin, and thymidine (HAT medium). Any of a number of myeloma cell lines can be used as a fusion partner according to standard techniques, e.g., the P3-NS1/1-Ag4-1, P3-x63-Ag8.653, or Sp2/O—Ag14 myeloma lines. These myeloma lines are available from ATCC (American Type Culture Collection, Manassas, Va.). Typically, HAT-sensitive mouse myeloma cells are fused to mouse splenocytes using polyethylene glycol (PEG). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind polypeptides or peptides, e.g., using a standard ELISA assay.

Alternative to preparing monoclonal antibody-secreting hybridomas, a monoclonal antibody can be identified and isolated by screening a recombinant combinatorial immunoglobulin library (e.g., an antibody phage display library) with the corresponding polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612).

Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al., 1991, *Bio/Technology* 9:1370–1372; Hay et al., 1992, *Hum. Antibod. Hybridomas* 3:81–85; Huse et al., 1989, *Science* 246:1275–1281; Griffiths et al., 1993, *EMBO J.* 12:725–734; Hawkins et al., 1992, *J. Mol. Biol.* 226:889–896; Clarkson et al., 1991, *Nature* 352:624–628; Gram et al., 1992, *PNAS* 89:3576–3580; Garrad et al., 1991, *Bio/Technology* 9:1373–1377; Hoogenboom et al., 1991, *Nuc. Acid Res.* 19:4133–4137; Barbas et al., 1991, *PNAS* 88:7978–7982; and McCafferty et al., 1990, *Nature* 348:552–55.

Additionally, recombinant antibodies to a polypeptide, such as chimeric monoclonal antibodies, can be made using standard recombinant DNA techniques. Such chimeric monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al., 1988, *Science* 240:1041–1043; Liu et al., 1987, *PNAS* 84:3439–3443; Liu et al., 1987, *J. Immunol.* 139:3521–3526; Sun et al., 1987, *PNAS* 84:214–218; Nishimura et al., 1987, *Canc. Res.* 47:999–1005; Wood et al., 1985, *Nature* 314:446–449; and Shaw et al., 1988, *J. Natl. Cancer Inst.* 80:1553–1559; S. L. Morrison, 1985, *Science* 229:1202–1207; Oi et al., 1986, *BioTechniques* 4:214; Winter U.S. Pat. No. 5,225,539; Jones et al., 1986, *Nature* 321:552–525; Verhoeyan et al., 1988, *Science* 239:1534; and Bcidler et al., 1988, *J. Immunol.* 141:4053–4060.

An antibody against a polypeptide (e.g., monoclonal antibody) can be used to isolate the corresponding polypeptide by standard techniques, such as affinity chromatography or immunoprecipitation. For example, antibodies can facilitate the purification of a natural polypeptide from cells and of a recombinantly produced polypeptide or peptide expressed in host cells. In addition, an antibody that binds to a polypeptide can be used to detect the corresponding protein (e.g., in a cell, cellular lysate, or cell supernatant) in order to evaluate the abundance, localization, or pattern of expression of the protein. Detection methods employing antibodies include well-established techniques, such as Western blot, dot blot, colony blot, ELISA, immunocytochemical, and immunohistochemical analysis.

Modulators

The N—CBZ-deprotecting enzyme polypeptides, polynucleotides, variants, modifications, or fragments thereof, can be used to screen for test agents (e.g., agonists, antagonists, inhibitors, or other modulators) that alter the levels or activity of the corresponding polypeptide. In addition, these molecules can be used to identify endogenous modulators that bind to polypeptides or polynucleotides in the *S. paucimobilis* cell. In one aspect of the present invention, a full-length N—CBZ-deprotecting enzyme polypeptide (e.g., SEQ ID NO:2) is used to identify modulators. Alternatively, variants or fragments of a N—CBZ-deprotecting enzyme polypeptide are used. Such fragments may comprise, for example, one or more domains of the polypeptides disclosed herein. A wide variety of assays may be used for these screens, including in vitro protein—protein binding assays, electrophoretic mobility shift assays, immunoassays, and the like.

The term "modulator" as used herein describes any test agent, molecule, protein, peptide, or compound with the capability of directly or indirectly altering the physiological function, stability, or levels of a polypeptide. Modulators that bind to polypeptides or polynucleotides of the invention are potentially useful in biotechnology or pharmaceutical applications, as described in detail herein. Test agents that are useful as modulators may encompass numerous chemical classes, though typically they are organic molecules, preferably small organic compounds having a molecular weight of more than 50 and less than about 2,500 daltons. Such molecules can comprise functional groups necessary for structural interaction with proteins, particularly hydrogen bonding, and typically include at least an amine, carbonyl, hydroxyl or carboxyl group, preferably at least two of the functional chemical groups. Test agents which can be used as modulators often comprise cyclical carbon or heterocyclic structures and/or aromatic or polyaromatic structures substituted with one or more of the above functional groups. Test agents can also comprise biomolecules including peptides, saccharides, fatty acids, steroids, purines, pyrimidines, derivatives, structural analogs, or combinations thereof.

Test agents finding use as modulators may include, for example, 1) peptides such as soluble peptides, including Ig-tailed fusion peptides and members of random peptide libraries (see, e.g., Lam et al., 1991, *Nature* 354:82–84; Houghten et al., 1991, *Nature* 354:84–86) and combinatorial chemistry-derived molecular libraries made of D- and/or L-configuration amino acids; 2) phosphopeptides (e.g., members of random and partially degenerate, directed phosphopeptide libraries, see, e.g., Songyang et al, (1993) *Cell* 72:767–778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules.

Test agents and modulators can be obtained from a wide variety of sources including libraries of synthetic or natural compounds. Synthetic compound libraries are commercially available from, for example, Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich Chemical Company, Inc. (Milwaukee, Wis.). Natural compound libraries comprising bacterial, fungal, plant or animal extracts are available from, for example, Pan Laboratories (Bothell, Wash.). In addition, numerous means are available for random and directed synthesis of a wide variety of organic compounds and biomolecules, including expression of randomized oligonucleotides.

Alternatively, libraries of natural compounds in the form of bacterial, fungal, plant and animal extracts can be readily produced. Methods for the synthesis of molecular libraries are readily available (see, e.g., DeWitt et al., 1993, *Proc. Natl. Acad. Sci. USA* 90:6909; Erb et al., 1994, *Proc. Natl. Acad. Sci. USA* 91:11422; Zuckermann et al., 1994, *J. Med. Chem.* 37:2678; Cho et al., 1993, *Science* 261:1303; Carell et al., 1994, *Angew. Chem. Int. Ed. Engl.* 33:2059; Carell et al., 1994, *Angew. Chem. Int. Ed. Engl.* 33:2061; and in Gallop et al., 1994, *J. Med. Chem.* 37:1233). In addition, natural or synthetic compound libraries and compounds can be readily modified through conventional chemical, physical and biochemical means (see, e.g., Blondelle et al., 1996, *Trends in Biotech.* 14:60), and may be used to produce combinatorial libraries. In another approach, previously identified pharmacological agents can be subjected to directed or random chemical modifications, such as acylation, alkylation, esterification, amidification, and the analogs can be screened for -modulating activity.

Numerous methods for producing combinatorial libraries are known in the art, including those involving biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer, or small molecule libraries of compounds (K. S. Lam, 1997, *Anticancer Drug Des.* 12:145).

Libraries may be screened in solution (e.g., Houghten, 1992, *Biotechniques* 13:412–421), or on beads (Lam, 1991 *Nature* 354:82–84), chips (Fodor, 1993 *Nature* 364:555–556), bacteria or spores (Ladner U.S. Pat. No. 5,223,409), plasmids (Cull et al., 1992 *Proc. Natl. Acad. Sci. USA* 89:1865–1869), or on phage (Scott and Smith, 1990, *Science* 249:386–390; Devlin, 1990, *Science* 249:404–406; Cwirla et al., 1990, *Proc. Natl. Acad. Sci. USA* 97:6378–6382; Felici, 1991, *J. Mol. Biol.* 222:301–310; Ladner, supra).

Where the screening assay is a binding assay, a polypeptide, polynucleotide, analog, or fragment thereof, may be joined to a label, where the label can directly or indirectly provide a detectable signal. Various labels include radioisotopes, fluorescers, chemiluminescers, enzymes, specific binding molecules, particles, e.g. magnetic particles, and the like. Preferred fluorescent labels include, for example, Cy3, Cy5, GFP (e.g., EGFP, DsRed, dEFP, etc. (CLONTECH, Palo Alto, Calif.)), Alexa, BODIPY, fluorescein (e.g., FluorX, DTAF, and FITC), rhodamine (e.g., TRITC), auramine, Texas Red, AMCA blue, and Lucifer Yellow. Preferred isotope labels include $^3$H, $^{14}$C, 32 P, $^{35}$S, $^{36}$Cl, $^{51}$Cr, $^{58}$Co, $^{59}$Co, $^{59}$Fe, $^{90}$Y, $^{125}$I, $^{131}$I, and $^{186}$Re. Non-limiting examples of enzyme labels include peroxidase, β-glucuronidase, β-D-glucosidase, β-D-galactosidase, urease, glucose oxidase plus peroxidase, and alkaline phosphatase (see, e.g., U.S. Pat. Nos. 3,654,090; 3,850,752 and 4,016,043). Enzymes can be conjugated by reaction with bridging molecules such as carbodiimides, diisocyanates, glutaraldehyde, and the like. Enzyme labels can be detected visually, or measured by calorimetric, spectrophotometric, fluorospectrophotometric, amperometric, or gasometric techniques. Other labeling systems, such as avidin/biotin, Tyramide Signal Amplification (TSA™), and digoxin/anti-digoxin, are known in the art, and are commercially available (see, e.g., ABC kit, Vector Laboratories, Inc., Burlingame, Calif.; NEN® Life Science Products, Inc., Boston, Mass.). For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc., that are used to facilitate optimal protein—protein binding and/or reduce non-specific or background interactions. Reagents that improve the efficiency of the assay, such as protease inhibitors, nuclease inhibitors, anti-microbial agents, etc., may be used. The components are added in any order that produces the requisite binding. Incubations are performed at any temperature that facilitates optimal activity, typically between 4° and 40° C. Incubation periods are selected for optimum activity, but may also be optimized to facilitate rapid high-throughput screening. Normally, between 0.1 and 1 hr will be sufficient. In general, a plurality of assay mixtures is run in parallel with different agent concentrations to obtain a differential response to these concentrations. Typically, one of these concentrations serves as a negative control, i.e. at zero concentration or below the level of detection.

To perform cell-free screening assays, it may be desirable to immobilize either the polypeptide, polynucleotide, variant, or fragment to a surface to facilitate identification of modulators that bind to these molecules, as well as to accommodate automation of the assay. For example, a fusion protein comprising a polypeptide and an affinity-tag can be produced as described in detail herein. In one embodiment, a GST-fusion protein comprising a polypeptide is adsorbed onto glutathione sepharose beads (Sigma Chemical, St. Louis, Mo.) or glutathione-derivatized microtiter plates. Cell lysates (e.g., containing $^{35}$S-labeled polypeptides) are added to the polypeptide-coated beads under conditions to allow complex formation (e.g., at physiological conditions for salt and pH). Following incubation, the polypeptide-coated beads are washed to remove any unbound polypeptides, and the amount of immobilized radiolabel is determined. Alternatively, the complex is dissociated and the radiolabel present in the supernatant is determined. In another approach, the beads are analyzed by SDS-PAGE to identify -binding polypeptides.

Various binding assays can be used to identify modulators that alter the function or levels of a polypeptide. Such assays are designed to detect the interaction of test agents with polypeptides, polynucleotides, variants, or fragments thereof. Interactions may be detected by direct measurement of binding. Non-limiting examples of useful binding assays are detailed as follows. Modulators that bind to polypeptides, polynucleotides, functional equivalents, or fragments thereof, can be identified using real-time Bimolecular Interaction Analysis (BIA; Sjolander et al., 1991, *Anal. Chem.* 63:2338–2345; Szabo et al., 1995, *Curr. Opin. Struct. Biol.* 5:699–705; e.g., BIAcore™; LKB Pharmacia, Sweden). Modulators can also be identified by scintillation proximity assays (SPA, described in U.S. Pat. No. 4,568,649). Binding assays using mitochondrial targeting signals (Hurt et al., 1985, *EMBO J.* 4:2061–2068; Eilers and Schatz, 1986, *Nature* 322:228–231) a plurality of defined polymers synthesized on a solid substrate (Fodor et al., 1991, *Science* 251:767–773) may also be employed.

Two-hybrid systems may be used to identify modulators (see, e.g., U.S. Pat. No. 5,283,317; Zervos et al., 1993, *Cell* 72:223–232; Madura et al., 1993, *J. Biol. Chem.* 268: 12046–12054; Bartel et al., 1993, *Biotechniques* 14:920–924; Iwabuchi et al., 1993, *Oncogene* 8:1693–1696; and Brent WO 94/10300). Alternatively, three-hybrid (Licitra et al., 1996, *Proc. Natl. Acad. Sci. USA* 93:12817–12821), and reverse two-hybrid (Vidal et al., 1996, *Proc. Natl. Acad. Sci. USA* 93:10315–10320) systems may be used. Commercially available two-hybrid systems such as the CLONTECH Matchmaker™ systems and protocols (CLONTECH Laboratories, Inc., Palo Alto, Calif.) are also useful (see also, A. R. Mendelsohn et al., 1994, *Curr. Op. Biotech.* 5:482; E. M. Phizicky et al., 1995, *Microbiological Rev.* 59:94; M. Yang et al., 1995, *Nucleic Acids Res.* 23:1152; S. Fields et al., 1994, *Trends Genet.* 10:286; and U.S. Pat. Nos. 6,283,173 and 5,468,614).

Several methods of automated assays have been developed in recent years so as to permit screening of tens of thousands of test agents in a short period of time. High-throughput screening methods are particularly preferred for use with the present invention. The binding assays described herein can be adapted for high-throughput screens, or alternative screens may be employed. For example, continuous format high throughput screens (CF-HTS) using at least one porous matrix allows the researcher to test large numbers of test agents for a wide range of biological or biochemical activity (see U.S. Pat. No. 5,976,813 to Beutel et al.). Moreover, CF-HTS can be used to perform multi-step assays.

Alternatively, interactions with test agents may be detected by indirect indicators of binding, such as stabilization/destabilization of protein structure, or activation/inhibition of biological function.

EXAMPLES

The examples as set forth herein are meant to exemplify the various aspects of the present invention and are not intended to limit the invention in any way.

Example 1

Selective Techniques for Isolation of Microrganisms

A selective culture technique was used to isolate microorganisms that able to utilize N-α-CBZ-L-lysine as a sole source of nitrogen. Soil samples were collected from various sites in New Jersey. About a gram of soil samples suspended in 5 mL of water, mixed thoroughly and samples were allowed to settle. The supernatant solutions from various samples were inoculated in a medium A (2% glucose, 0.2% $KH_2PO_4$, 0.2% $K_2HPO_4$, 0.01% $MgSO_4$, 0.001% $FeSO_4$, 0.001% $ZnSO_4$, pH 7.0) containing 1% N-α-CBZ-L-lysine. After 4 days of growth when medium became turbid, cultures were transferred to the above medium containing 1.5% agar contained in petri plates. From this enrichment culture techniques eight different types of colonies were isolated. One culture (Z-2) was further identified as *Sphingomonas paucimobilis* strain and was deposited in American Type Culture Collection, Rockville, Md. as *Sphingomonas paucimobilis* strain ATCC 202027. This culture was used as a source of CBZ-deprotecting enzyme.

Example 2

Growth of *Sphingomonas paucimobilis*

*Sphingomonas paucimobilis* was grown on N-α-CBZ-L-phenylalanine or [4S-(4α,7α,10aβ)]-Octahydro-5-oxo-4-[[(phenylmethoxy)carbonyl]amino]-7H-pyrido-[2,1-b] [1,3] thiazepine-7-carboxylic acid, methyl ester (Compound A) as sole source of nitrogen. The *Sphingomonas paucimobilis* culture was inoculated in a medium A containing 1% N-α-CBZ-L-phenylalanine or 1% Compound A. After 2 days of growth, cultures were transferred to the medium A containing 1% N-α-CBZ-L-phenylalanine or 1% BMS199541, and 1.5% agar contained in petri plates. The colonies were isolated from the petri plates were grown in 100 mL of medium B (0.015% yeast extract, 2% glucose, 0.2% $KH_2PO_4$, 0.2% $K_2HPO_4$, 0.01% $MgSO_4$ and 0.2% NaCl, pH 7) containing 1% N-αCBZ-L-phenylalanine and or 1% Compound A. Culture was grown at 28° C. and 280 RPM for 24 hours on a rotary shaker. Vials were prepared (1 mL culture in a 2 mL vial) from this culture and were stored at −70° C. for future use.

One vial (containing 1 mL of *Sphingomonas paucimobilis* in medium B) was used to inoculate 100 mL of medium B. Cultures were grown at 28° C. and 280 RPM for 48 hours on a rotary shaker. Cells were harvested by centrifugation at 18,000×g for 15 minutes, and stored at −70° C. until further use.

Example 3

Biotransformation Using Whole Cells

In this process, the *Sphingomonas paucimobilis* was grown in 25 mL of medium B containing 25 mg of substrate (Compound A or CBZ-L-Phenylalanine) in a 250-mL flask. The flask was incubated at 28° C. and 250 rpm on a shaker. After 48 hours of biotransformation, the cells were removed by centrifugation. The supernatant containing the product [4S-(4α,7α,10aβ)]-Octahydro-5-oxo-4-amino-7H-pyrido-[2,1-b] [1,3]thiazepine-7-carboxylic acid, methyl ester (Compound B) or L-Phenylalanine was analyzed by HPLC. The results are shown in the table 1.

TABLE 1

| Substrate | Product | % Conversion |
|---|---|---|
| Compound A | Compound B | 100 |
| CBZ-L-Phenylalanine | L-phenylaline | 100 |

HPLC Analysis

HPLC analysis was performed using a Hewlett-Packard (HP) 1090 instrument with a Vydac C-18 reverse phase column. The mobile phase solvent A containing 0.1% trifluoroacetic acid (TFA) in water and solvent B containing 0.1% TFA in 70% acetonitrile: 30% water. The following gradient of solvent A and B was used for the separation of substrates and products:

0–15 min: 50% B, 15–25 min: 100% B, 25–26 min: 0% B, and 26–30 min: 0% B. The flow rate was 1 mL/min. The column temperature was ambient, and the detection wavelength was at 215 nm. Under these conditions, the retention times for Compound A, Compound B, CBZ-L-Phenylalanine and L-Phenylalanine are 15.48 min., 7.28 min., 16.99 min. and 7.35 min., respectively. All other CBZ-containing compounds were also analyzed using these conditions.

Example 4

Deprotection of CBZ Using Cell Extracts of *Sphingomonas paucimobilis* ATCC 202027

Preparation of Cell Extract of *Sphingomonas paucimobilis* ATCC 202027

Preparation of cell extracts were carried out at 4–7° C. Cells were washed with 50 mM potassium phosphate buffer, pH 7.0, and the washed cells (100 g) were suspended in 500 mL of buffer A (50 mM phosphate buffer, pH 7.0 containing 10% glycerol, and 2 mM DTT). To the cell suspensions, 1 mM phenylmethylsulfonyl fluoride (PMSF) solution in isopropanol was added. Cell suspensions (20% W/V, wet cells) were passed through a Microfluidizer (Microfluidics, Inc) at 12,000 psi (two passages) and disintegrated cells were centrifuged at 25,000×g for 30 min at 4° C. The supernatant solution obtained after centrifugation is referred to as cell extract.

CBZ-Deprotection Using Cell Extract

The cell extracts was used in deprotecting the CBZ-group from various compounds. It was useful in deprotecting CBZ-groups in various processes. Various D and L-CBZ-protected amino acids were incubated with the cell extract at 42° C. for 18–20 hours. The reactions were stopped by addition of 2 volumes of 50% acetonitrile containing 0.4% trifluro acetic acid (TFA). The results shown in table 2 indicate that the enzyme is specific in hydrolyzing the CBZ-group from CBZ-protected L-amino acids.

TABLE 2

| Substrate | Product | % Conversion |
|---|---|---|
| N-α-CBZ-L-tyrosine | L-tyrosine | 100 |
| N-α-CBZ-D-tyrosine | D-tyrosine | 1.58 |
| O-α-CBZ-L-tyrosine | L-tyrosine | 100 |
| N-α-CBZ-L-Leucine | L-Leucine | 100 |
| N-α-CBZ-D-Leucine | D-Leucine | 1.2 |
| N-α-CBZ-L-phenylalanine | L-phenylalanine | 100 |
| N-α-CBZ-D-phenylalanine | D-phenylalanine | 0 |
| N-α-CBZ-L-Lysine | L-Lysine | 52 |
| N-ε-CBZ-D-Lysine | D-Lysine | 7 |
| N-α-ε-(CBZ)$_2$-L-Lysine | L-Lysine | 24 |
| N-α-CBZ-L-Proline | L-Proline | 100 |
| N-α-CBZ-D-Proline | D-Proline | 0 |
| Compound A | Compound B | 95 |

Example 5

Purification of CBZ-Deprotecting Enzyme and the Use of Purified Enzyme in the Deprotection of CBZ-Group from Cbz-Containing Compounds Enzyme Assays Compound A or CBZ-phenylalanine at 0.5 mg was incubated with 0.4 mL of cell extract/fractions in 50 mM phosphate buffer, pH 7 at 45° C. for 18 hours. The reaction is stopped by the addition 1 ml of 50% acetonitrile containing 0.4% TFA. The samples were filtered and analyzed by HPLC for product and starting material.

Protein Assay

The Bio-Rad protein assay was used to determine protein concentration. The assay was performed according to the manufacturer (Bio-Rad) protocol.

Purification of the Enzyme

All the purification steps were carried out at room temperature. The purification of the enzyme was carried out using CBZ-L-phenylalanine as the substrate. The cell extract, prepared as above, was batch adsorbed with DEAE-cellulose (pre-equilibrated with buffer A) for 2 hours. The follow-through, which contained the active enzyme, was precipitated with ammonium sulfate (516 g/L) with constant stirring for 2 hours. The resulting precipitate obtained by centrifugation (15,000 rpm at 4° C.) was solubilized in buffer A containing 1M ammonium sulfate, loaded on to phenylsepharose (20 mL column which was pre-equlibriaiated with buffer A containing 1M ammonium sulfate). The column was sequentially washed with the buffer A containing 1M ammonium sulfate, 0.5M ammonium sulfate and 0.2M ammonium sulfate. Finally, the enzyme was eluted with buffer A. The fractions containing active enzyme were pooled (30 mL) and concentrated with Amicon PM-10 membrane (8 mL). The enzyme was then loaded on to S-200 gel-filtration column (400 mL column). The enzyme was eluted with buffer A with a flow rate of 0.8 mL/min. With these steps the enzyme was purified more than 150-fold with a specific activity of 13.9 units/mg protein (table 3). The unit is defined as μmole of product formed/min/mg of protein. The enzyme is a dimeric protein with a molecular weight of ~154,000 daltons with a subunit molecular weight of 45,000 daltons, as determined by SDS-PAGE.

TABLE 3

Purification of CBZ-Deprotecting Enzyme

| Step | Volume mL | Activity U/mL | Protein mg/mL | Sp.Activ. U/mg | Purification fold |
|---|---|---|---|---|---|
| Cell Extract | 500 | 0.142 | 1.8 | 0.08 | 1.00 |
| DE52-Flow Through | 700 | 0.183 | 0.58 | 0.32 | 4.00 |
| Ammonium Sulfate Precipitation | 60 | 2.496 | 7.45 | 0.34 | 4.25 |
| Phenylsepharose column | 28 | 0.117 | 0.13 | 0.90 | 11.41 |
| S-200 Gel-filtration column | 7 | 0.139 | 0.01 | 13.90 | 176.20 |

The purified enzyme prepared as described in this section has been used to deprotect CBZ-containing compounds as shown in table 4.

TABLE 4

| Substrate | Product | % Conversion |
|---|---|---|
| Compound A | Compound B | 100 |
| CBZ-L-Phenylalanine | L-phenylalanine | 100 |

Example 6

Enzymatic Deprotection of 250 mg Prep Batch of Compound A

The cell extract was prepared as described in the above section. To a 250 mL of cell extract, 250 mg Compound A was added and incubated at 28° C. and 95 rpm. After 40 hours of reaction, 250 mL of acetonitrile was added. The substrate and the product were analyzed by HPLC. The molar yield for Compound B was 87%.

Example 7

Enzymatic Deprotection of CBZ-Containing Compounds

The cell extract prepared as described in the earlier section from *Sphingomonas paucimobilis* ATCC 202027 was used to deprotect [(3S)-Hexahydro-2-oxo-1-[2-oxo-2-(1-pyrrolidinyl)ethyl]-1H-azepin-3-yl]carbamic acid, phenylmethyl ester (Compound C) resulting in the formation of (S)-1-[(3-Aminohexahydro-2-oxo-1H-azepin-1-yl)acetyl]pyrrolidine (Compound D).

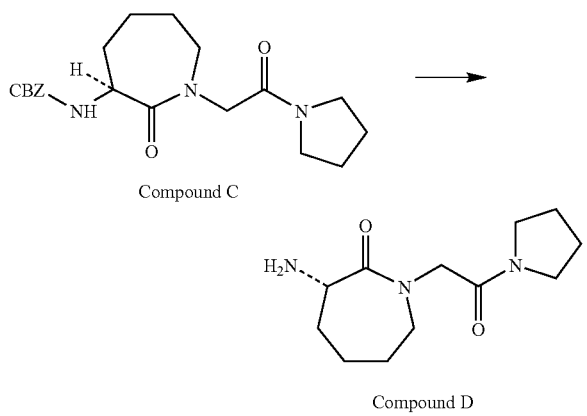

Compound C

Compound D

Example 8

Enzymatic Deprotection of CBZ-Containing Compounds

The cell extract prepared as described in the earlier section from *Sphingomonas paucimobilis* ATCC 202027 was used to deprotect 6-[(phenylmethoxy)carbonyl]amino] hexahydro-2,2-dimethyl-7-oxo-1H-azepine-1-acetic acid, ethyl ester hydrochloride 1 to 6-Aminohexahydro-2,2-dimethyl-7-oxo-1H-azepine-1-acetic acid, ethyl ester, hydrochloride (Compound E).

Example 9

Purification and Amino Acid Sequencing of *S. paucimobilis* N—CBZ-Deprotecting Enzyme The enzyme purification and characterization of N—CBZ-deprotecting enzyme is described above and in WO 02/053724. Sequencing of the N-terminal and internal peptides was carried out by Argo BioAnalytica, Inc., Morris Plains, N.J.

Example 10

Identification of the Gene Encoding *S. paucimobilis* N—CBZ-Deprotecting Enzyme

*Sphingomonas paucimobilis* (ATCC 202027) was grown in 50 mL LB medium (media composition per liter: 10 g Bacto tryptone, 5 g Bacto yeast extract and 5 g NaCl) at 37° C. for 16 hours at 200 rpm in a shaker. The cells were harvested by centrifugation and the chromosomal DNA was prepared using the procedure described in Ausubel et al. (eds.) Current Protocols in Molecular Biology, vol. 2, section 13.11.2 (1991), John Wiley and Sons, New York.

Degenerate PCR primers based on the N-terminal region (SPN: 5'-ATG GTI CAR CCI ACI CCI ACI CCI CAR WC-3') (SEQ ID NO:4) and an internal peptide (SPI4: 5'-CCR AAR TCY TCI CCI CCC ATI ACI GCI GG-3') (SEQ ID NO: 5), where "A"=adenosine, "C"=cytosine, "G"=guanosine, "T"=thymidine, "W"=A+T, "R"=A+G, "Y"=C+T, and "I"=deoxyinosine, were used to amplify the gene using genomic DNA as target. The amplification conditions included incubation at 94° C. for 1 min, followed by 30 cycles at 94° C. for 0.5 min; 50° C. for 0.5 min; and 72° C. for 0.5 min using a Hybaid PCR Express thermocycler [ThermoHybaid US, Franklin, Mass.]. The resultant 1000-base pair (bp) PCR fragment was cloned into cloning vector pZero2.1 using the TA Cloning Kit (Invitrogen, Carlsbad, Calif.), which contains the pZero2.1 vector.

To isolate the gene encoding CBZ deprotection, *S. paucimobilis* chromosomal DNA was cleaved with restriction endonucleases ApaI, BamHI, DraI, EcoRI, EcoRV, HindIII, KpnI, NotI, PstI, SpeI, XbaI and XhoI under conditions recommended by the manufacturer (Promega, Madison, Wis.). Ca. 3 μg of each digested DNA was electrophoresed at 20 v for 18 hr through a 0.8% agarose gel in TAE buffer (0.04 M Trizma base, 0.02 M acetic acid, and 0.001 M EDTA, pH 8.3) containing 0.5 μg/ml ethidium bromide. Fragments were transferred to a Hybond N+ nylon filter (Amersham Pharmacia, Piscataway, N.J.) using a VacuGene blotting apparatus (Amersham Pharmacia). The recombinant plasmid containing the 1000-bp PCR fragment was digested with EcoRI and the fragment isolated using the QIAquick Gel Extraction kit (Qiagen, Chatsworth, Calif.) according to the manufacturer's protocol. The fragment was labeled with digoxygenin-dUTP using the PCR DIG Probe Kit (Roche Biochemicals, Indianapolis, Ind.) for use as a probe in Southern hybridizations.

Hybridization to the filter containing *Sphingomonas paucimobilis* chromosomal digests, washing, and detection were performed according to materials and directions supplied with the DIG High Prime DNA Labeling and Detection Starter Kit II (Roche Biochemicals). Stringent wash conditions were 1×SSC (20×SSC is 173.5 g NaCl, 88.2 g NaCl, pH 7.0) and 0.1% sodium dodecyl sulfate at 68° C. A single hybridizing fragment was visible in ApaI, DraI, EcoRI, HindIII, KpnI, NotI, SpeI, XbaI and XhoI digests; a 4.8 kb NotI fragment was chosen for further work. Ca. 10 μg of *S. paucimobilis* chromosomal DNA was cleaved with 25 U NotI for 2 hr at 37° C. in a final volume of 0.1 ml using the buffer recommended by the manufacturer (Promega, Madison, Wis.). The DNA was electrophoresed on a 0.8% agarose gel in TAE buffer at 20 v for 18 hr. Fragments between 4.2 and 5.2 kb were identified by comparison to a 1 kb Plus DNA ladder (Invitrogen) and excised using a scalpel. The DNA was isolated from the agarose using the QIAquick Gel Extraction Kit and ligated to NotI-cleaved pZero2 vector DNA in a 2:1 molar ratio in a total volume of 10 μL at 22° C. for 2 hr with 1 U T4 DNA ligase (Invitrogen). Two μL of ligated DNA was transformed by electroporation into 0.04 mL competent *E. coli* DH10B cells (Invitrogen). SOC medium was immediately added (0.96 mL; SOC is [per liter], 0.5% yeast extract, 2% tryptone, 10 mM NaCl, 2.5 mM KCl, 10 mM MgCl$_2$, 10 mM MgSO$_4$, and 20 mM glucose) and the cells incubated in a shaker for 1 hr at 37° C., 225 rpm. Cells were spread onto a 132 mm Hybond N+ membrane circle placed on top of LB kanamycin agar medium (kanamycin was purchased from Sigma Chemicals, St. Louis, Mo. and used at a final concentration of 50 μg/ml)

and incubated at 37° C. for 20 hr. The colonies were replicated onto two fresh filters that were placed on top of LB kanamycin agar medium and incubated at 37° C. for 4 hr. Colonies were lysed in situ by placing the filters on a piece of Whatman 3MM paper saturated with 0.5 M NaOH for 5 min. The filters were dried for 5 min on Whatman paper, then neutralized on 3MM paper soaked in 1.0 M Tris-HCl, pH 7.5 for 2 min, and dried for 2 min. Membranes were placed on top of 3MM paper saturated with 1.0 M Tris-HCl, pH7.0/1.5 M NaCl for 10 min. DNA was crosslinked to the filters by exposure to ultraviolet light in a Stratagene UV Stratalinker 2400 set to "auto crosslink" mode (Stratagene, La Jolla, Calif.). Cell debris was removed from the membranes by immersion in 3×SSC/0.1% SDS and wiping the surface with a wetted Kimwipe, then incubating in the same solution heated to 65° C. for 3 hr with agitation. Filters were rinsed with dH$_2$O and used immediately or wrapped in SaranWrap® and stored at 4° C. Hybridization with the 1000 bp *S. paucimobilis* gene probe, washing, and detection was performed as described above using reagents included in the DIG Wash and Block Kit (Roche). Putative hybridizing colonies were picked from the master plate, inoculated into SOC medium containing kanamycin, and grown at 37° C. for 24 hr at 250 rpm. Cells from 1 ml of cell culture were pelleted by centrifugation. Plasmid DNA was isolated using the QIAprep Spin Miniplasmid Kit (Qiagen). The presence of the desired region of DNA was verified by PCR using plasmid DNA as the target DNA with primers SPN and SPI4. Six of the eight colonies gave the expected PCR product. An aliquot of these six plasmids digested with NotI confirmed the presence of a 4.8-kb fragment.

Example 11

Determination and Analysis of the Nucleotide Sequence of *S. paucimobilis* CBZ-Gene A series of random in vitro transposon insertions in and around the cloned 4.8 kb NotI fragment present in pZero2 was created using the Genome Priming System (GPS™-1) according to the manufacturer's instructions (New England Biolabs, Beverly, Mass.). The transposon carries primer sites that permit sequencing of both strands of target DNA. Sequencing was performed using the BigDye terminator kit and an Applied Biosystems model 377 DNA sequencing unit (Perkin-Elmer, Foster City, Calif.). The complete nucleotide sequence of the coding region (SEQ ID NO:1) and amino acid sequence (SEQ ID NO:2) are shown below. The coding region is 1281 bp in length and encodes a 426-amino acid protein (MW 45,695 daltons).

```
        M   V   Q   P   T   P   T   P   Q   S   E   L
  1   ATG GTT CAG CCC ACC CCC ACG CCG CAG AGT GAA CTG

P   G   L   I   A   R   D   M   E   G   L   M
 37   CCC GGC CTG ATC GCC AGG GAC ATG GAG GGG CTG ATG

T   L   Y   R   D   L   H   A   N   P   E   L
 73   ACC CTC TAT CGC GAC CTG CAC GCC AAT CCC GAA CTC

S   L   Q   E   V   N   T   A   A   K   L   A
109   TCG CTG CAG GAG GTG AAC ACC GCC GCC AAG CTG GCC

K   R   L   K   A   M   K   F   D   V   T   E
145   AAG CGC CTG AAA GCG ATG AAG TTC GAC GTG AGG GAA

K   V   G   G   T   G   V   V   A   V   M   K
181   AAG GTC GGC GGC AGG GGG GTC GTC GCG GTG ATG AAG

N   G   S   G   P   V   L   L   I   R   A   D
217   AAT GGC TCT GGC CCC GTG GTG CTC ATT GGC GCC GAG

N   D   C   L   P   V   V   E   Q   T   G   L
253   ATG GAC GGC CTG CCC GTG GTC GAG CAG ACC GGC CTC

D   F   A   S   K   V   R   T   K   T   P   E
289   GAC TTC GCT TCC AAG GTC CGC ACC AAG ACG CCA GAG

G   V   E   T   G   V   M   H   A   C   G   H
325   GGG GTC GAG ACC GGC GTG ATG CAC GCC TGC GGC CAT

D   T   H   M   T   A   F   I   E   T   A   K
361   GAC ACC CAC ATG ACC GCC TTC ATC GAG ACC GGC AAG

L   L   S   S   Q   K   D   K   W   K   G   T
397   GTG GTG TCC AGC GAG AAG GAC AAG TGG AAG GGG ACG

L   V   M   I   L   Q   P   A   E   E   V   G
433   CTG GTG ATG ATC GTC GAG CCC GCC GAG GAA GTG GGC

K   G   A   R   D   M   L   E   D   G   L   Y
469   AAG CCC GGC GGG GAG ATG GTG GAG GAG GGG CTC TAG

T   R   F   P   R   P   T   H   A   I   A   F
505   ACG GGG TTG GGG GGG GGG AGG GAT GGG ATG GGG TTG

H   D   A   A   N   L   Q   A   G   V   V   G
541   GAT GAG GGG GGG AAT GTG GAG GGG GGG GTG GTG GGG

Y   T   P   G   Y   A   L   A   N   V   D   S
577   TAT AGG GGG GGG TAT GGG GTG GGG AAT GTG GAG AGG

V   D   I   V   V   K   G   L   G   G   H   G
613   GTG GAT ATG GTG GTG AAG GGG CTG GGG GGG GAT GGG

A   Y   P   Q   T   T   R   D   P   I   V   L
649   GGG TAT GGG GAG AGG AGG GGG GAG GGA ATG GTG GTG

G   S   R   I   V   T   S   L   Q   T   L   V
685   GGT TGG GGG ATG GTT AGG TGG GTG GAG AGT TTG GTG

S   R   E   Q   D   P   Q   D   P   A   V   V
721   AGG GGG GAA GAG GAT GGG GAG GAT GGG GGG GTG GTG

T   V   G   S   F   Q   A   G   A   K   H   N
757   AGG GTG GGG AGG TTC CAC GGG GGG GGG AAG GAG AAG

I   I   P   D   Q   A   L   L   L   L   T   V
793   ATG ATG CCG GAG GAG GGG GTG GTG GTG GTC AGG GTG

R   S   Y   S   D   E   T   R   A   K   L   I
829   GGG AGG TAT TGG GAG GAG AGG GGG GGG AAG GTG ATG

K   G   I   E   R   I   A   R   G   E   A   I
865   AAG GGG ATC GAG CGG ATC GCC CGT GGC GAG GCG ATT

A   A   C   V   P   D   D   K   M   P   V   V
```

```
                                              S   V   K   D   E   F   T   P   S   T   Y   N
901 GCG GCG GGC GTG CCC GAC GAC AAG ATG CCG GTG GTC        937 AGC GTC NAG GAC GAG TTC ACC CCG TCC ACC TAC NAT

P   P   E   F   A   E   Q   M   G   A   L   L
973 CCG CCC GAA TTT GCC GNA CAG ATG GGC GCG CTG CTC

K   G   H   F   A   E   G   R   V   V   K   T
1009 AAG GGG CAT TTC GCC GAG GGC CGC GTG GTC AAG ACC

P   A   V   M   G   G   E   D   F   G   R   F
1045 CCG GCG GTG ATG GGC GGC GAG GAT TTC GGC CGC TTC

Y   R   A   D   K   S   I   N   S   F   I   F
1081 TAC CGC GCC GAC AAG TCG ATC AAC AGC TTC ATC TTC

W   V   G   G   V   P   A   D   K   M   A   A
1117 TGG GTC CCC GGC GTG CCG GCG GAC AAG ATG GCG GCG

A   Q   A   G   Q   I   T   L   P   S   L   H
1153 GCG CAG GCC CGC CAG ATC ACC CTG CCC TCG CTG CAC

S   P   F   W   A   P   E   A   D   K   V   I
1189 AGT CCG TTC TGG GCG CCG GAG GCC GAC AAG GTG ATC

A   T   A   S   E   A   M   T   V   L   A   M
1225 GCC ACC GCC AGC GAG GCG ATG ACC GTC CTC GCC ATG

D   I   L   K   K   D   *
1261 GAT ATC CTC AAG AAG GAT TGA
```

The N—CBZ-deprotecting enzyme coding region (in bold) along with the surrounding non-coding region is shown below in SEQ ID NO:3.

```
AATGGTCAGACGAAACGGTTCGCTGCGCCCTGACCGTGAAGGAAGCCATTTATTTGACCT
CGCAGCCTCACGCCGGAAAAAGCAGCGGGAGACCGAACGGGCCAGACAGTGCGGTCCCA
TCCATCGTCATCGATACAGATAGCCCGGGCTGCAATCGATCCCGACCGCTATCGATCGCTC
GGCAGCCGAATGGCGGCGGCCAAATGGGAAACATTGGGGCTGTTTGCCTATATAACTGCG
ACNCAGGCCTATTGGACCGACGACACGACCTCCTTGCATTTCAAGGATGAAGGCTGGTTC
GGCAAGGACACCAACAATCTGGGCATCGACAAGCTGACGCACGCTTTCAACGCCTATCTC
TTCGCCGAATTTCTGGGCGCACGCATCGCCCGCAAGACTGATGACCGGGCTGCCGCCGCC
TTGCCGGCTGCCCTGCTGTCGACCGCGCTGCAATTCTACGGCGAATTATGGGACGGCCATA
AAACGGACAGCGGCTTCTCCTACCAAGACATTGTCTTCAACACGGCCGGCGCCGCCTTTTC
CGTGCTGCGGCACACCGTACCGGGGCTGGAGGAGAAGCTCGATTTCCGGCTGATGATGGT
GCCCAATTCCAACGTCTACAGCTTCAAGGGGAAGCGCCATTATGAACAGCAGCATTTCCT
GCTGTCGCTCGAACTGGCCGGGTTCAGGAAATTGGAGGCCACCCCTTTCCGGCTCGTCGA
ACTGCAGGTCGGCTATCGTGGCAAGGATTTCACCCTTGCCGACCGCGCCGCCGGTATCCCC
CCGAAACGCGACATCTTCTTCGGCGTCGCGCTCAACATCAAGCAACTCTTCTTCAAGAACA
ATCGGTCGCGCGTCGGCCGCATGATCGGCAGCGGCCTCAACTATTTCCAGCTCCCCTATAC
CGGCATCTATGATTATTACTGAACCTTGCCGCGCGCGCCGGCCAGCATCGTAACAATCCCC
CTTTAACACCCGTAAAATCCCCCTATGCTCCTGCCCAGCAAGGGAGATTCAATCATATGCG
CCACGCGCTCACGGCCTTTCTGGCCGCTGTCAGCTTTTCGTCCATGGCCGTCGCCCAAACC
CCGACCGCGCCGCCGCCGGCTCAGCCGTCCATGGTTCAGCCCACCCCCACGCCGCAGA
GTGAACTGCCCGGCCTGATCGCCAGGGACATGGAGGGGCTGATGACCCTCTATCGC
GACCTGCACGCCAATCCCGAACTCTCGCTGCAGGAGGTGAACACCGCCGCCAAGCT
GGCCAAGCGCCTGAAAGCGATGAAGTTCGACGTGACCGAAAAGGTCGGCGGCACCG
GCGTCGTCGCGGTGATGAAGAATGGCTCTGGCCCCGTCCTCCTCATTCGCGCCGACA
TGGACGGCCTGCCCGTGGTCGAGCAGACCGGCCTCGACTTCGCTTCCAAGGTCCGC
ACCAAGACGCCAGAGGGGGTCGAGACCGGCGTGATGCACGCCTGCGGCCATGACAC
```

-continued

```
CCACATGACCGCCTTCATCGAGACCGCCAAGCTGCTGTCCAGCCAGAAGGACAAGTG

GAAGGGCACGCTGGTGATGATCCTCCAGCCGGCCGAGGAAGTGGGCAAGGGCGCCC

GCGACATGCTGGAGGACGGGCTCTACACCCGCTTCCCGCGCCCGACCCATGCCATC

GCCTTCCATGACGCCGCCAATCTCCAGGCCGGCGTCGTCGGCTATACGCCGGGCTAT

GCCCTCGCCAATGTCGACAGCGTCGATATCGTGGTGAAGGGGCTGGGCGGCCATGG

CGCCTATCCGCAGACGACCCGCGACCCAATCGTGCTGGGTTCGCGCATCGTTACCTC

GCTGCAGACTTTGGTCAGCCGCGAACAGGATCCGCAGGATCCCGCCGTGGTGACCG

TCGGCAGCTTCCAGGCCGGCGCCAAGCACAACATCATCCCCGACCAGGCGCTGCTG

CTGCTGACCGTGCGCAGCTATTCGGACGAGACCCGCGCCAAGCTGATCAAGGGGAT

CGAGCGGATCGCCCGTGGCGAGGCGATTGCGGCGGGCGTGCCCGACGACAAGATGC

CGGTGGTCAGCGTCAAGGACGAGTTCACCCCGTCCACCTACAATCCGCCCGAATTTG

CCGAACAGATGGGCGCGCTGCTCAAGGGGCATTTCGCCGAGGGCCGCGTGGTCAAG

ACCCCGGCGGTGATGGGCGGCGAGGATTTCGGCCGCTTCTACCGCGCCGACAAGTC

GATCAACAGCTTCATCTTCTGGGTCGGCGGCGTGCCGGCGGACAAGATGGCGGCGG

CGCAGGCCGGCCAGATCACCCTGCCCTCGCTGCACAGTCCGTTCTGGGCGCCGGAG

GCCGACAAGGTGATCGCCACCGCCAGCGAGGCGATGACCGTCCTCGCCATGGATAT

CCTCAAGAAGGATTGAGCTTATACGCTGACCGCGCAGCGGCGCCGATGGACCTCCATCA

GCGCCAGCGCGGTCAGCGCCACGCCCAGGCCCAGGATCATATCGATCAGATAATGGGTGC

CCTCCACCGGCGTGGACAGCAGCATCGCCGCGTTGAGCGCGACGATCGGCCAGCGCAGCG

CCGCGATCCGCCAGCCCGCCGCAATATACAGAACCGCCGCCGCGGTATGGAAGCTGGGCG

CCGACACGATGCCGCGCAACTGCCCCAGGTCGATGGCATGGACCGCATGCGTCCGCAGCG

CCGGGATCAGCCCCTGCTGCCACAATTCGCTTTCGGGCATGTAGCGGATCGGTTCGTGCCA

CAGATAAGAGAATGGCCCAACCGCCGGCATCAGGCTGAACAGGATCAGGGTGATGACCG

CCGCCAGCCAGAAGCTGGCGATGAAGCGCCAGGCCCGTTCCTGCTCGCCCGCCCGCGCCA

TGCACCATAGCAGCAGCGCCGGCGTCACATAGATGCTGCGATAGGCGGCCGTTTCCAGGA

ATTGGAGTGTCCGGTGCGACGCGGTCAGCCGATACCAATGGAGCCAGTCAAACCCCAGCG

CCGCGTCGATCCGCTGCAAGGTCGCATCGGCATAGCCATGGGTCAGCGCTGCCACGGGAT

AGCTGGCCGCCGCCCCCATGACCGATATCAGCGTGAACAGGCCGACATAGGTGGCAAATG

GCGCCACCGTCTCGGCATGGCGCCAGCCGCTGCGCGGCAGGCCAAAGCGCAACCCCAGCA

ACAGCGCCGCCGCCGCGCCATAGGCGATGCTGCTCACCTGCCAGAAATCGATGCGCAGAT

CCGCCATGTCCAGCAGCAGGGCGAGCAGCACCATGCTCACGCCCAGGGCCGCCAGAAAAT

GCCGCCGGATCGCCAATGATCGCGTGACAATCGGCACCAGACGCGCCGTCTGCGCGGCAA

CAGGCTCAGCCAGGGGCCAGGAGGTTTCGATCGACGGCATCACGCATATGTCCGGGAAGA

AAGGCGGAAAGGCCGCCCTTCCGCCTCCCGTGCTTAAGCTGCGATGAACCGTTGCATAAC

GCCCCTGTCAGGGCTGCAACAACCAGCCCGCGCCACCGCCCAGCGCGATGATCGCCGGCA

TGCTCCACCGCCCCTTGATCCGCCAGGCGCAGAGCGCGCCGACCAGGAAGATCAGGCCGG

CGGCCCAGAGCCGGTCCGCCCGCATCGCCGCCGCCCAACCCAGTTGCACCAGGGTCGCAG

CGATGACGCCGACCACC
```

Example 12

S. paucimobilis N—CBZ-Deprotecting Enzyme Subcloning and Expression in E. coli To facilitate PCR-based cloning of the CBZ-deprotecting enzyme gene into expression vector pBMS2000 (U.S. Pat. No. 6,068,991 to Liu, et al), oligonucleotide primers containing the 5' and 3' end of the gene along with compatible restriction endonuclease cleavage sites were prepared:
a) (5' end of gene)
5'CGGATTCCATATGGTTCAGCCCACCCCAC 3' (SEQ ID NO:6)
NdeI
b) (3' end of gene; anti-sense)
5' GCACCCGGGCTCAATCCTTCTTGAGGATAT 3' (SEQ ID NO:7)
SmaI High-fidelity amplification of the CBZ-deprotecting gene was carried out in 4×25 µl aliquots, each consisting of 1X Z-Taq reaction buffer (Pan Vera Corporation, Madison, Wis.), 0.2 µM each deoxynucleotide triphosphate (dATP, dCTP, dGTP, dTTP), 0.4 nM each oligonucleotide, 2.5 U Z-Taq DNA polymerase (Pan Vera), and 10 pg plasmid DNA containing the cloned CBZ-deprotecting gene. The amplification condition was 94° C., 4 min followed by 25 cycles at 94° C., 1 min; 50° C., 1 min; and 72° C., 1.5 min using a Perkin-Elmer Model 480 thermocycler with autoextension. The PCR samples were electrophosed on a 1.0% TAE agarose gel for 2 hr at 100 v. The 1200-bp PCR fragment containing the CBZ-deprotecting gene was excised from the gel and purified using the QIAquick Gel Extraction Kit. Concentrations of the isolated DNA was estimated by electrophoresis vs. the Low Molecular Weight mass ladder (Invitrogen). Purified DNA was digested with 20 units of NdeI for 2 hr at 37° C. in a total volume of 20 µl, then diluted to 40 µl with water, followed by digestion with 20 units of SmaI at 30° C. for 2 hours. The expression vector pBMS2000 was similarly cleaved with these endonucleases in parallel. Digested DNA samples were electrophoresed on a 1.0% TAE agarose gel for 2 hr at 100 v. The 1200- and 4700-bp fragments containing the CBZ-deprotecting gene and pBMS2000 DNA, respectively, were excised from the gel and purified using the QIAquick Gel Extraction Kit. The concentrations of the isolated DNAs were estimated by electrophoresis vs. the Low Molecular Weight mass ladder (Invitrogen). Ligation of the PCR fragment and pBMS2000 and transformation were carried out as described in Section 1A. Cells containing plasmid were selected on LB agar containing 20 µg/ml neomycin at 37° C. for 20 hr. Plasmids with the desired insert were screened by colony PCR in capillary tubes using the RapidCycler (Idaho Technology, Salt Lake City, Utah). Each reaction consisted of 50 mM Tris-HCl (pH 8.3), 4 mM $MgCl_2$, 0.25 mg/ml bovine serum albumin, 2% sucrose 400, 0.1 mM cresol red, 0.4 nM each primer above, 2.5 U Taq DNA polymerase (Promega). The reaction mix was distributed as 10 µL aliquots into wells of a round-bottom microtiter plate. A neomycin-resistant colony was picked using a disposable plastic inoculation needle and swirled into the liquid, then transferred to LB-neomycin agar. Reactions were drawn into a 30-µL capillary tube and flame-sealed at both ends. Cells were lysed and DNA denatured by holding at 94° C. for 30 sec; amplification took place for 30 cycles at 94° C., 0 sec; 40° C., 0 sec, and 72° C., 60 sec. Samples were electrophoresed on a 1.0% TAE agarose gel for 2 hr, 100 v. Seven samples out of 17 tested had a strong band at 1100 bp. One colony containing this plasmid (named pBMS2000-cbz) was chosen for further study.

The recombinant plasmid was transformed into four additional E. coli strains by electroporation: BL21(DE3), DH10B, JM110, and W3110-M25. The E. coli strain BL21 (DE3) transformed with pBMS2000-cbz was designated SC 16501, with one particular vial lot designated SC 16501 V2A. Transformed cells were selected on LB-neomycin agar medium and a single colony in each instance inoculated into 10 mL MT3 medium (1.0% NZAmine A, 2.0% Yeastamin, 2.0% glycerol, 0.6% $Na_2HPO_4$, 0.3% $KH_2PO_4$, 0.125% $(NH_4)_2SO_4$, and 0.0246% $MgSO_4$) containing 30 µg/mL neomycin. The cultures were incubated at 28° C., 250 rpm, for 20 hr, then diluted in fresh medium to an $OD_{600}$ nm of 0.25 and incubated under the same conditions until the $OD_{600}$ was 1.0±0.1. IPTG was added to a final concentration of 0.1 mM and the cultures grown at the above conditions for 20 hr. Cells were pelleted by centrifugation (5,000×g) for 7 min, the medium removed, and washed with an equal volume ice cold 50 mM $KPO_4$ buffer (pH 7.3)/2 mM dithiothreitol. The cells were again pelleted and the wet cell weight recorded.

The cloned CBZ-deprotecting gene was deposited in E. coli cells SC 16501 V2A containing pBMS2000-cbz at the American Type Culture Collection (ATCC), 10801 University Boulevard, Manassas, Va. 20110-2209, on Mar. 12, 2003 as ATCC Accession No. PTA-5051 according to the terms of the Budapest Treaty.

Example 13

Use of Recombinant Enzyme in Deprotecting CBZ-Group from L-Amino-Acids

To demonstrate the utility of the recombinant enzyme, the cloned enzyme was used in the deprotection of CBZ-L-phe. The reaction contained 0.5 mg of CBZ-L-phe and 0.5 ml of cell extract from E. coli BL21(DE3)(pBMS2000-cbz) that expressed the deprotecting enzyme. Preparation of cell extract was as follows: 2 g of recombinant cells were suspended in 10 mL buffer A (50 mM phosphate buffer, pH 7.5, 1 mM EDTA), sonicated for 2 minutes (20 seconds pulse on and 30 seconds pulse off) using a model 550 Sonic Dismembrator from Misonix Inc., Farmingdale, N.Y. The disintegrated cells were centrifuged for 15 min at 8000 rpm at 4° C. and the resulting supernatant, referred to as a cell extract, was used for these studies. The reactions were carried out in a culture tube at 28° C. After 1 hr, samples were quenched with 1 ml of acetonitrile and analyzed by HPLC (described earlier). There was complete deprotection of the substrate using recombinant enzyme, while no reaction took place in the absence of recombinant enzyme.

The contents of all patents, patent applications, published articles, books, reference manuals, texts and abstracts cited herein are hereby incorporated by reference in their entirety to more fully describe the state of the art to which the present invention pertains. Any patent application to which this application claims priority is also incorporated by reference herein.

As various changes can be made in the above compositions and methods without departing from the scope and spirit of the invention, it is intended that all subject matter

What is claimed is:

1. An isolated nucleic acid comprising a nucleotide sequence encoding the amino acid sequence of SEQ ID NO:2, or the complement thereof.

2. An isolated nucleic acid comprising a fragment of the nucleotide sequence of claim 1, wherein said fragment encodes at least 300 contiguous residues of the amino acid sequence of SEQ ID NO:2, and wherein said fragment encodes a polypeptide having catalytic activity, wherein said catalytic activity comprises deprotection of a N-carbobenzyloxy-protected amino acid.

3. The isolated nucleic acid of claim 1 comprising: (a) the nucleotide sequence SEQ ID NO:1; (b) nucleotides 1–1278 of SEQ ID NO:1; (c) the nucleotide sequence of SEQ ID NO:3; (d) the complement of (a), (b) or (c); or (e) a nucleotide sequence that differs from (a), (b), (c) or (d) due to degeneracy of the genetic code.

4. An isolated nucleic acid comprising the nucleotide sequence, encoding a N-carbobenzyloxy-deprotecting enzyme polypeptide, deposited as ATCC Accession Number PTA-5051.

5. An isolated nucleic acid which hybridizes under stringent conditions to any one of: (a) the nucleotide sequence SEQ ID NO:1; (b) nucleotides 1–1278 of SEQ ID NO:1; (c) the nucleotide sequence of SEQ ID NO:3; (d) the complement of (a), (b) or (c); or (e) a nucleotide sequence that differs from (a), (b), (c) or (d) due to degeneracy of the genetic code, wherein said isolated nucleic acid encodes a polypeptide having catalytic activity, wherein said catalytic activity comprises deprotection of a N-carbobenzyloxy-protected amino acid, and wherein said stringent hybridization conditions are hybridization in 50% formamide, 5×Denhardt's solution, 5×SSPE, and 0.2% SDS at 42° C., followed by washing in 0.1×SSPE and 0.1% SDS at 65° C.

6. A vector comprising the isolated nucleic acid of claim 1, 3 or 5.

7. A host cell comprising the vector of claim 6, wherein the host cell is selected from the group consisting of bacterial, fungal, insect, mammalian, and plant cells.

8. A method for producing a recombinant polypeptide comprising:
   a) culturing the host cell of claim 7 under conditions suitable for the production of a recombinant polypeptide; and
   b) recovering the recombinant polypeptide from the host cell or host cell culture, thereby producing the recombinant polypeptide.

9. The isolated nucleic acid of claim 2 wherein the N-carbobenzyloxy-protected amino acid is an L-amino acid.

10. The isolated nucleic acid of claim 9 wherein the N-carbobenzyloxy-protected amino acid is N-carbobenzyloxy-L-phenylalanine.

11. The isolated nucleic acid of claim 2 wherein said catalytic activity comprises deprotection of 10 to 100% of the N-carbobenzyloxy-protected amino acid.

12. The isolated nucleic acid of claim 11 wherein said catalytic activity comprises deprotection of 80 to 100% of the N-carbobenzyloxy-protected amino acid.

13. The isolated nucleic acid of claim 2 wherein said fragment encodes at least 400 contiguous residues of the amino acid sequence of SEQ ID NO:2.

14. The isolated nucleic acid of claim 13 wherein said fragment encodes at least 415 contiguous residues of the amino acid sequence of SEQ ID NO:2.

15. An isolated nucleic acid molecule comprising a nucleotide sequence sharing at least 95% sequence identity with SEQ ID NO: 1, wherein said nucleotide sequence encodes a polypeptide having catalytic activity, and wherein said catalytic activity comprises deprotection of a N-carbobenzyloxy-protected amino acid.

* * * * *

SEQUENCE LISTING

<160> NUMBER OF SEQ ID NOS: 7

<210> SEQ ID NO 1
<211> LENGTH: 1281
<212> TYPE: DNA
<213> ORGANISM: Sphingomonas paucimobilis

<400> SEQUENCE: 1

```
atggttcagc ccaccccac gccgcagagt gaactgcccg gcctgatcgc cagggacatg      60
gagggctga tgaccctcta tcgcgacctg cacgccaatc ccgaactctc gctgcaggag     120
gtgaacaccg ccgccaagct ggccaagcgc ctgaaagcga tgaagttcga cgtgaccgaa     180
aaggtcggcg gcaccggcgt cgtcgcggtg atgaagaatg gctctggccc cgtcctcctc     240
attcgcgcca catggacgg cctgcccgtg gtcgagcaga ccggcctcga cttcgcttcc     300
aaggtccgca ccaagacgcc agaggggtc gagaccggcg tgatgcacgc ctgcggccat     360
gacacccaca tgaccgcctt catcgagacc gccaagctgc tgtccagcca aaggacaag     420
tggaagggca cgctggtgat gatcctccag ccggccgagg aagtgggcaa gggcgcccgc     480
gacatgctgg aggacgggct ctacacccgc ttcccgcgcc cgacccatgc catcgccttc     540
catgacgccg ccaatctcca ggccggcgtc gtcggctata cgccgggcta tgccctcgcc     600
aatgtcgaca gcgtcgatat cgtggtgaag gggctgggcg gccatggcgc ctatccgcag     660
acgacccgcg acccaatcgt gctgggttcg cgcatcgtta cctcgctgca gactttggtc     720
agccgcgaac aggatccgca ggatcccgcc gtggtgaccg tcggcagctt ccaggccggc     780
gccaagcaca acatcatccc cgaccaggcg ctgctgctgc tgaccgtgcg cagctattcg     840
gacgagaccc gcgccaagct gatcaagggg atcgagcgga tcgcccgtgg cgaggcgatt     900
gcggcgggcg tgcccgacga caagatgccg gtggtcagcg tcaaggacga gttcaccccg     960
tccacctaca atccgcccga atttgccgaa cagatgggcg cgctgctcaa ggggcatttc    1020
gccgagggcc gcgtggtcaa gaccccggcg gtgatgggcg gcgaggattt cggccgcttc    1080
taccgcgccg acaagtcgat caacagcttc atcttctggg tcggcggcgt gccggcggac    1140
aagatggcgg cggcgcaggc cggccagatc accctgccct cgctgcacag tccgttctgg    1200
gcgccggagg ccgacaaggt gatcgccacc gccagcgagg cgatgaccgt cctcgccatg    1260
gatatcctca agaaggattg a                                             1281
```

<210> SEQ ID NO 2
<211> LENGTH: 426
<212> TYPE: PRT
<213> ORGANISM: Sphingomonas paucimobilis

<400> SEQUENCE: 2

```
Met Val Gln Pro Thr Pro Thr Pro Gln Ser Glu Leu Pro Gly Leu Ile
1               5                   10                  15

Ala Arg Asp Met Glu Gly Leu Met Thr Leu Tyr Arg Asp Leu His Ala
                20                  25                  30

Asn Pro Glu Leu Ser Leu Gln Glu Val Asn Thr Ala Ala Lys Leu Ala
            35                  40                  45

Lys Arg Leu Lys Ala Met Lys Phe Asp Val Thr Glu Lys Val Gly Gly
```

```
            50                  55                  60
Thr Gly Val Val Ala Val Met Lys Asn Gly Ser Gly Pro Val Leu Leu
 65                  70                  75                  80

Ile Arg Ala Asp Met Asp Gly Leu Pro Val Val Glu Gln Thr Gly Leu
                 85                  90                  95

Asp Phe Ala Ser Lys Val Arg Thr Lys Thr Pro Glu Gly Val Glu Thr
                100                 105                 110

Gly Val Met His Ala Cys Gly His Asp Thr His Met Thr Ala Phe Ile
                115                 120                 125

Glu Thr Ala Lys Leu Leu Ser Ser Gln Lys Asp Lys Trp Lys Gly Thr
130                 135                 140

Leu Val Met Ile Leu Gln Pro Ala Glu Val Gly Lys Gly Ala Arg
145                 150                 155                 160

Asp Met Leu Glu Asp Gly Leu Tyr Thr Arg Phe Pro Arg Pro Thr His
                165                 170                 175

Ala Ile Ala Phe His Asp Ala Ala Asn Leu Gln Ala Gly Val Val Gly
                180                 185                 190

Tyr Thr Pro Gly Tyr Ala Leu Ala Asn Val Asp Ser Val Asp Ile Val
                195                 200                 205

Val Lys Gly Leu Gly Gly His Gly Ala Tyr Pro Gln Thr Thr Arg Asp
210                 215                 220

Pro Ile Val Leu Gly Ser Arg Ile Val Thr Ser Leu Gln Thr Leu Val
225                 230                 235                 240

Ser Arg Glu Gln Asp Pro Gln Asp Pro Ala Val Val Thr Val Gly Ser
                245                 250                 255

Phe Gln Ala Gly Ala Lys His Asn Ile Ile Pro Asp Gln Ala Leu Leu
                260                 265                 270

Leu Leu Thr Val Arg Ser Tyr Ser Asp Glu Thr Arg Ala Lys Leu Ile
                275                 280                 285

Lys Gly Ile Glu Arg Ile Ala Arg Gly Glu Ala Ile Ala Ala Gly Val
290                 295                 300

Pro Asp Asp Lys Met Pro Val Val Ser Val Lys Asp Glu Phe Thr Pro
305                 310                 315                 320

Ser Thr Tyr Asn Pro Pro Glu Phe Ala Glu Gln Met Gly Ala Leu Leu
                325                 330                 335

Lys Gly His Phe Ala Glu Gly Arg Val Val Lys Thr Pro Ala Val Met
                340                 345                 350

Gly Gly Glu Asp Phe Gly Arg Phe Tyr Arg Ala Asp Lys Ser Ile Asn
                355                 360                 365

Ser Phe Ile Phe Trp Val Gly Val Pro Ala Asp Lys Met Ala Ala
370                 375                 380

Ala Gln Ala Gly Gln Ile Thr Leu Pro Ser Leu His Ser Pro Phe Trp
385                 390                 395                 400

Ala Pro Glu Ala Asp Lys Val Ile Ala Thr Ser Glu Ala Met Thr
                405                 410                 415

Val Leu Ala Met Asp Ile Leu Lys Lys Asp
                420                 425

<210> SEQ ID NO 3
<211> LENGTH: 3659
<212> TYPE: DNA
<213> ORGANISM: Sphingomonas paucimobilis
<220> FEATURE:
<221> NAME/KEY: misc_feature
<222> LOCATION: (243)..(243)
```

-continued

<223> OTHER INFORMATION: n is a, c, g, or t

<400> SEQUENCE: 3

```
aatggtcaga cgaaacggtt cgctgcgccc tgaccgtgaa ggaagccatt tatttgacct      60
cgcagcctca cgccggaaaa agcagcggga gaccgaacgg gccagacagt gcggtcccat     120
ccatcgtcat cgatacagat agcccgggct gcaatcgatc ccgaccgcta tcgatcgctc     180
ggcagccgaa tggcggcggc caaatgggaa acattggggc tgtttgccta tataactgcg     240
acncaggcct attggaccga cgacacgacc tccttgcatt tcaaggatga aggctggttc     300
ggcaaggaca ccaacaatct gggcatcgac aagctgacgc acgctttcaa cgcctatctc     360
ttcgccgaat ttctgggcgc acgcatcgcc cgcaagactg atgaccgggc tgccgccgcc     420
ttgccggctg ccctgctgtc gaccgcgctg caattctacg gcgaattatg ggacggccat     480
aaaacggaca gcggcttctc ctaccaagac attgtcttca cacggccgg cgccgccttt      540
tccgtgctgc ggcacaccgt accggggctg gaggagaagc tcgatttccg gctgatgatg     600
gtgcccaatt ccaacgtcta cagcttcaag gggaagcgcc attatgaaca gcagcatttc     660
ctgctgtcgc tcgaactggc cggggttcag aaattggagg ccacccctt ccggctcgtc       720
gaactgcagg tcggctatcg tggcaaggat ttcacccttg ccgaccgcgc cgccggtatc     780
cccccgaaac gcgacatctt cttcggcgtc gcgctcaaca tcaagcaact cttcttcaag     840
aacaatcggt cgcgcgtcgg ccgcatgatc ggcagcggcc tcaactattt ccagctcccc     900
tataccggca tctatgatta ttactgaacc ttgccgcgcg cgccggccag catcgtaaca     960
atccccttt aacacccgta aaatcccct atgctcctgc ccagcaaggg agattcaatc      1020
atatgcgcca cgcgctcacg gccttctgg ccgctgtcag cttttcgtcc atggccgtcg     1080
cccaaaccc gaccgcgccg ccgccggctc agccgtccat ggttcagccc accccacgc      1140
cgcagagtga actgcccggc ctgatcgcca gggacatgga ggggctgatg accctctatc    1200
gcgacctgca cgccaatccc gaactctcgc tgcaggaggt gaacaccgcc gccaagctgg    1260
ccaagcgcct gaaagcgatg aagttcgacg tgaccgaaaa ggtcggcggc accggcgtcg    1320
tcgcggtgat gaagaatggc tctggccccg tcctcctcat tcgcgccgac atggacggcc    1380
tgcccgtggt cgagcagacc ggcctcgact tcgcttccaa ggtccgcacc aagacgccag    1440
aggggtcga ccggcgtg atgcacgcct gcggccatga cacccacatg accgccttca      1500
tcgagaccgc caagctgctg tccagccaga aggacaagtg gaagggcacg ctggtgatga    1560
tcctccagcc ggccgaggaa gtgggcaagg gcgcccgcga catgctggag gacgggctct    1620
acacccgctt cccgcgcccg acccatgcca tcgccttcca tgacgccgcc aatctccagg    1680
ccggcgtcgt cggctatacg ccgggctatg ccctcgccaa tgtcgacagc gtcgatatcg    1740
tggtgaaggg gctgggcggc catgcgcct atccgcagac gacccgcgac ccaatcgtgc    1800
tgggttcgcg catcgttacc tcgctgcaga ctttggtcag ccgcgaacag gatccgcagg    1860
atcccgccgt ggtgaccgtc ggcagcttcc aggccggcgc caagcacaac atcatccccg    1920
accaggcgct gctgctgctg accgtgcgca gctattcgga cgagacccgc gccaagctga    1980
tcaaggggat cgagcggatc gcccgtggcg aggcgattgc ggcgggcgtg cccgacgaca    2040
agatgccggt ggtcagcgtc aaggacgagt tcacccccgtc cacctacaat ccgcccgaat   2100
ttgccgaaca gatgggcgcg ctgctcaagg ggcatttcgc cgagggccgc gtggtcaaga    2160
ccccggcggt gatgggcggc gaggatttcg gccgcttcta ccgcgccgac aagtcgatca    2220
acagcttcat cttctgggtc ggcggcgtgc cggcggacaa gatggcggcg gcgcaggccg    2280
```

-continued

```
gccagatcac cctgccctcg ctgcacagtc cgttctgggc gccggaggcc gacaaggtga    2340
tcgccaccgc cagcgaggcg atgaccgtcc tcgccatgga tatcctcaag aaggattgag    2400
cttatacgct gaccgcgcag cggcgccgat ggacctccat cagcgccagc gcggtcagcg    2460
ccacgcccag gcccaggatc atatcgatca gataatgggt gccctccacc ggcgtggaca    2520
gcagcatcgc cgcgttgagc gcgacgatcg gccagcgcag cgccgcgatc cgccagcccg    2580
ccgcaatata cagaaccgcc gccgcggtat ggaagctggg cgccgacacg atgccgcgca    2640
actgccccag gtcgatggca tggaccgcat gcgtccgcag cgccgggatc agcccctgct    2700
gccacaattc gctttcgggc atgtagcgga tcggttcgtg ccacagataa gagaatggcc    2760
caaccgccgg catcaggctg aacaggatca gggtgatgac cgccgccagc cagaagctgg    2820
cgatgaagcg ccaggcccgt tcctgctcgc ccgcccgcgc catgcaccat agcagcagcg    2880
ccggcgtcac atagatgctg cgataggcgg ccgtttccag gaattggagt gtccggtgcg    2940
acgcggtcag ccgataccaa tggagccagt caaacccag cgccgcgtcg atccgctgca    3000
aggtcgcatc ggcatagcca tgggtcagcg ctgccacggg atagctggcc gccgccccca    3060
tgaccgatat cagcgtgaac aggccgacat aggtggcaaa tggcgccacc gtctcggcat    3120
ggcgccagcc gctgcgcggc aggccaaagc gcaaccccag caacagcgcc gccgccgcgc    3180
cataggcgat gctgctcacc tgccagaaat cgatgcgcag atccgccatg tccagcagca    3240
gggcgagcag caccatgctc acgcccaggc ccgccagaaa atgccgccgg atcgccaatg    3300
atcgcgtgac aatcggcacc agacgcgccg tctgcgcggc aacaggctca gccagggggcc    3360 aggaggtttc gatcgacggc atcacgcata tgtccgggaa gaaaggcgga aaggccgccc    3420
ttccgcctcc cgtgcttaag ctgcgatgaa ccgttgcata cgcccctgt cagggctgca    3480 acaaccagcc cgcgccaccg cccagcgcga tgatcgccgg catgctccac cgccccttga    3540
tccgccaggc gcagagcgcg ccgaccagga agatcaggcc ggcggcccag agccggtccg    3600
cccgcatcgc cgccgcccaa cccagttgca ccagggtcgc agcgatgacg ccgaccacc     3659
```

<210> SEQ ID NO 4
<211> LENGTH: 29
<212> TYPE: DNA
<213> ORGANISM: Sphingomonas paucimobilis
<220> FEATURE:
<221> NAME/KEY: misc_feature
<222> LOCATION: (6)..(29)
<223> OTHER INFORMATION: n = deoxyinosine (I)
<220> FEATURE:
<221> NAME/KEY: misc_feature
<222> LOCATION: (9)..(29)
<223> OTHER INFORMATION: r = a or g
<220> FEATURE:
<221> NAME/KEY: misc_feature
<222> LOCATION: (28)..(29)
<223> OTHER INFORMATION: w = a or t

<400> SEQUENCE: 4

```
atggtncarc cnacnccnac nccncarwc                                        29
```

<210> SEQ ID NO 5
<211> LENGTH: 29
<212> TYPE: DNA
<213> ORGANISM: Sphingomonas paucimobilis
<220> FEATURE:
<221> NAME/KEY: misc_feature
<222> LOCATION: (3)..(29)
<223> OTHER INFORMATION: r = a or g
<220> FEATURE:

-continued

```
<221> NAME/KEY: misc_feature
<222> LOCATION: (9)..(29)
<223> OTHER INFORMATION: y = c or t
<220> FEATURE:
<221> NAME/KEY: misc_feature
<222> LOCATION: (12)..(29)
<223> OTHER INFORMATION: n = deoxyinosine (I)

<400> SEQUENCE: 5
ccraartcyt cnccncccat nacngcngg                                29

<210> SEQ ID NO 6
<211> LENGTH: 30
<212> TYPE: DNA
<213> ORGANISM: Artificial Sequence
<220> FEATURE:
<223> OTHER INFORMATION: Artificial Sequence = Oligonucleotide Primer

<400> SEQUENCE: 6
cggattccat atggttcagc ccaccccac                                30

<210> SEQ ID NO 7
<211> LENGTH: 30
<212> TYPE: DNA
<213> ORGANISM: Artificial Sequence
<220> FEATURE:
<223> OTHER INFORMATION: Artificial Sequence = Oligonucleotide Primer

<400> SEQUENCE: 7
gcacccgggc tcaatccttc ttgaggatat                               30
```